United States Patent
Johansson et al.

(10) Patent No.: US 10,781,197 B2
(45) Date of Patent: Sep. 22, 2020

(54) SULFONAMIDE ANALOGUES OF GALIELLALACTONE

(71) Applicant: GLACTONE PHARMA DEVELOPMENT AB, Helsingborg (SE)

(72) Inventors: Martin Johansson, Helsingborg (SE); Olov Sterner, Malmö (SE)

(73) Assignee: GLACTONE PHARMA DEVELOPMENT AB, Helsingborg (SE)

( * ) Notice: Subject to any disclaimer, the term of this patent is extended or adjusted under 35 U.S.C. 154(b) by 0 days.

(21) Appl. No.: 16/466,028

(22) PCT Filed: Dec. 5, 2017

(86) PCT No.: PCT/EP2017/081505
§ 371 (c)(1),
(2) Date: Jun. 2, 2019

(87) PCT Pub. No.: WO2018/104295
PCT Pub. Date: Jun. 14, 2018

(65) Prior Publication Data
US 2020/0087274 A1   Mar. 19, 2020

(30) Foreign Application Priority Data
Dec. 5, 2016   (SE) ..................................... 1651594

(51) Int. Cl.
| | |
|---|---|
| *C07D 307/93* | (2006.01) |
| *C07D 401/12* | (2006.01) |
| *C07D 409/12* | (2006.01) |
| *C07D 413/12* | (2006.01) |
| *A61K 31/365* | (2006.01) |
| *A61K 31/422* | (2006.01) |
| *A61K 31/443* | (2006.01) |
| *A61K 45/06* | (2006.01) |
| *A61K 31/381* | (2006.01) |

(52) U.S. Cl.
CPC .......... *C07D 307/93* (2013.01); *A61K 31/365* (2013.01); *A61K 31/381* (2013.01); *A61K 31/422* (2013.01); *A61K 31/443* (2013.01); *A61K 45/06* (2013.01); *C07D 401/12* (2013.01); *C07D 409/12* (2013.01); *C07D 413/12* (2013.01)

(58) Field of Classification Search
CPC .. C07D 307/93; C07D 401/12; C07D 409/12; C07D 413/12; A61K 31/365; A61K 31/422; A61K 31/443; A61K 45/06
See application file for complete search history.

(56) References Cited

U.S. PATENT DOCUMENTS 6,512,007 B1   1/2003  Baumgarten et al.

FOREIGN PATENT DOCUMENTS

| WO | 2012010555 A1 | 1/2012 |
| WO | 2015132396 A1 | 9/2015 |
| WO | 2016193332 A1 | 12/2016 |

OTHER PUBLICATIONS

International Search Report and Written Opinion for PCT/EP2017/081505 dated Feb. 5, 2018.
Johnston, P.A; Grandis, J.R. Mol Interv. 2011 11(1): 18-26.
Sansone, P; Bromberg, J. J Clin Oncol. 2012;30(9):1005-14.
Miklossy, G.; Hilliard, T.S.; Turkson, J. Nat Rev Drug Discov. 2013 12(8):611-29.
Yu, H.; Lee, H.; Herrmann, A.; Buettner, R.; Jove, R. Nat Rev Cancer. 2014 14(11):736-46.
STAT Inhibitors in Cancer, Ed. Alister C. Ward, Humana Press, 2016.
Weidler et al in FEBS Letters 2000, 484, 1-6.
Hellsten et al reported in Prostate 68:269-280 (2008.
Don-Doncow, N.; Escobar, Z.; Johansson, M.; Kjellström, S.; Garcia, V.; Munoz, E.; Sterner, O.; Bjartell, A.; Hellsten, R.; J. Biol. Chem. 2014 289(23):15969-15978.

(Continued)

*Primary Examiner* — Timothy R Rozof
(74) *Attorney, Agent, or Firm* — Renner, Otto, Boisselle & Sklar, LLP

(57) ABSTRACT

Disclosed are sulfonamide analogues of galiellactone of formula (I) as STAT3-inhibitors for use in the treatment of a STAT3 signaling related disorder, e.g. solid cancers, hematological cancers, benign tumors, hyperproliferative diseases, inflammations, autoimmune diseases, graft or transplant rejections, delayed physiological function of grafts or transplants, neurodegenerative diseases and viral infections. The sulfonamide comprises a cyclic substituent.

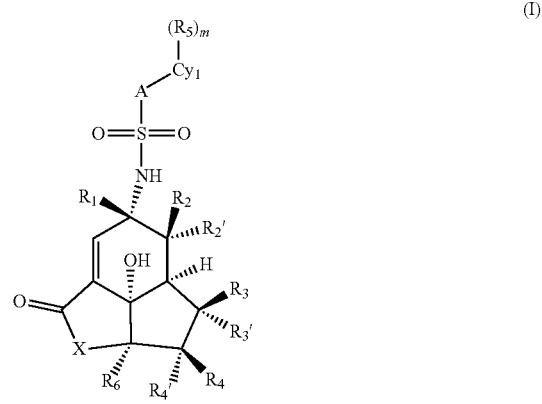

19 Claims, 1 Drawing Sheet

(56) References Cited

OTHER PUBLICATIONS

GPA500 inhibits the STAT3 activity and suppresses ENZ-resistant Prostate Cancer in vitro. Daksh Thaper, Sepideh Vahid, Jennifer Bishop, Martin Johansson and Amina Zoubeidi. AACR Annual Meeting 2015, Abstract nr 728.
Rudolph et al Cytokine. Jan. 2013;61(1):285-96).
Hausding et al Int Immunol. Jan. 2011;23(1):1-15).
Organic Letters 12, 22, 5100-5103 2010.
J. Org. Chem. 2014, 79, 8668-8677.
Org. Biomol. Chem. 2008, 6, 4299-4314.
Von Nussbaum F et al "The high-intrinsic Diels-Alder Reactivity of(–)-Galiellalactone; Generating Four Quatery Carbon Centers under Mild Conditions" EP journal of organ Chemistry Jul. 1, 2004 vol. 2004; p. 2783-2790.
Journal of Antibiotics 55,7, 663-665 2002.

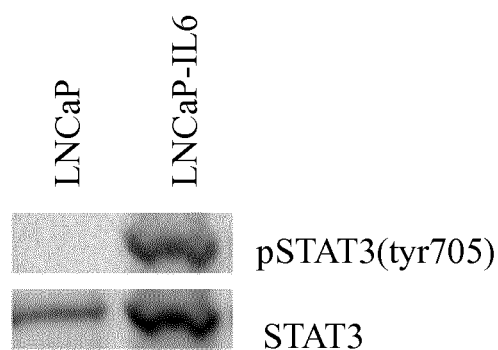

SULFONAMIDE ANALOGUES OF GALIELLALACTONE

This application is a national phase of International Application No. PCT/EP2017/081505 filed Dec. 5, 2017 and published in the English language, which claims priority to Swedish Application No. 1651594-2 filed Dec. 5, 2016, both of which are hereby incorporated by reference.

TECHNICAL FIELD

The present invention relates to analogues of galiellalactone, pharmaceutical compositions comprising such compounds, and a method of treating or alleviating conditions, in particular cancer, by use of such compounds.

BACKGROUND

Cancer is a heterogeneous disease. A treatment should be adopted for a given type of cancer as determined by the location and genetic makeup of the tumor. However, all forms of cancer show some fundamental similarities including uncontrolled growth and self-renewal and this is in some ways driven by the pattern of gene expression. Since many different signals, regardless of cause, converge on transcription factors, and since the activation of transcription factors is a nodal point for gene transcription, transcription factors should be convergent targets for treating cancer.

Transcription factors are essential cellular components mediating different extracellular signals, including developmental and environmental, by binding to transcription responsive elements in the genome and thereby initiating the transcription of specific target genes. Aberrant transcription factor function is often associated with different diseases and leads to either increased or excessive gene transcription. As many signals and activating mechanisms converge on single transcription factors they could make efficient drug targets, e.g. for treatment of cancer.

Latent cytoplasmic transcription factors (LCTFs) are transcription factors that reside in the cytoplasm in an inactive form until they are activated through an external signal often in the form of a cell surface receptor-ligand interaction. Among these transcription factors are the family of Signal Transducer and Activator of Transcription (STAT) proteins. The STAT proteins have dual roles as they can act as both transducers of signals through the cytoplasm and function as transcription factors in the nucleus.

STAT3 is one of 6 members of the STAT family of transcriptions factors. It is an approx. 770 amino acid long protein with 6 subunits or domains; N-terminal, coiled-coil, DNA-binding, linker, SH2 and transactivation domains. STAT3 is activated by cytokine, growth factor and non-receptor mediated signaling. The canonical mechanism of STAT3 activation is kinase mediated phosphorylation of tyrosine 705 (Y705) in the SH2 domain. This triggers a reciprocal recognition of two SH2 domains of STAT3 monomers leading to the formation of a STAT3 dimer. This dimer is translocated to the nucleus, aided by importins, and transcription of target genes, through binding to DNA, is activated. On its way to the nucleus STAT3 can be further modified through serine phosphorylation, lysine acetylation or Small Ubiquitin-like Modifier (SUMO) protein attachment and these modifications serve to modulate the transcriptional activity of STAT3

STAT3 activation and dimerization through phosphorylation can be achieved through at least three responses. STAT3 can be phosphorylated by JAK kinases that are constitutively bound to cytokine receptors. Upon ligand binding, the receptors aggregate and the JAK2 proteins undergo reciprocal activation through phosphorylation and they can then recruit and activate STAT3 through binding to the SH2 domain. Alternatively, growth factor receptors can directly recruit and associate with STAT3 leading to STAT3 activation through their receptor tyrosine kinase activity. Finally, non-receptor kinases, e.g. Src family kinases and Abl, can also activate STAT3. In addition, non-phosphorylated STAT3 can be transported into the nucleus and participate in transcription probably by binding to other proteins to form functional heteromeric transcription factors.

In the nucleus STAT3 can interact with several other proteins including other transcription factors e.g. NF-κB.

STAT3 can also be activated by phosphorylation on serine 727 by various kinases. This phosphorylation leads to enhanced transcriptional activity. Constitutively phosphorylated serine 727 is widespread in cells from patients suffering from chronic lymphocytic leukemia (CLL).

Since STAT3 activation under normal conditions is transient, multiple negative feedback systems exist. STAT3 signaling is tightly regulated and it is not constitutively activated in normal tissue. Several endogenous negative regulators for STAT3 signaling have been found and these include Suppressor of cytokine signaling (SOCS, that bind to and inactivate JAKs) and protein inhibitor of activated STAT (PIAS). SOCS is also a gene product of STAT3 transcription demonstrating this as a negative feedback loop. Loss of PIAS or SOCS function or reduced expression will increase STAT3 activation and mutations of these regulatory factors have been found in diseases related to increase STAT3 signaling.

Finally, STAT3 is dephosphorylated in the nucleus by different phosphatases and the dephosphorylated STAT3 monomers are transported out of the nucleus where they once again reside latent.

The target genes of STAT3 transcription are involved in cell growth and cell cycle regulation (e.g. Cyclin D1, c-Myc, p27), apoptosis (e.g. Mcl-1, survivin, Bcl-2, and Bcl-xL), angiogenesis (VEGF), metastasis (e.g. MMP-2, MMP-3) and immune.

STAT3 can be activated by cytokines and growth factors including IL6, LIF, IL-10, IL-1, IL-12, EGF, TGFalpha, PDGF and G-CSF and various tyrosine and serine kinases including JAK, JAK2, JAK3, TYK2, Src, Src, Lck, Hck, Lyn, Fyn, Fgr, EGFR, ErbB-2, Grb2, JNK, P38MAPK and ERK.

STAT3 is an experimentally validated target in several cancer forms, including leukemia, lymphomas, multiple myeloma, breast cancer, prostate carcinoma, lung cancer (non-small-cell), renal cell carcinoma lung cancer, hepatocellular carcinoma, cholangiocarcinoma, ovarian carcinoma, pancreatic adenocarcinoma, melanoma, head and neck squamous cell carcinoma (Johnston, P. A; Grandis, J. R. Mol Interv. 2011 11(1): 18-26). STAT3 signaling is involved in proliferation, survival, metastasis, drug resistance and migration of cancer cells and it also links inflammation and cancer. STAT3 also contributes to a tumor-promoting microenvironment that can play an important role in both tumor initiation and malignant progression This has been demonstrated in numerous studies in vitro, using primary cells or immortalized cell lines, or in vivo using xenograft models (cf. e.g. Sansone, P; Bromberg, J. J Clin Oncol. 2012; 30(9):1005-14, and Miklossy, G.; Hilliard, T. S.; Turkson, J. Nat Rev Drug Discov. 2013 12(8): 611-29) and as such is believed to be an ideal target for cancer therapy (Yu, H.; Lee, H.; Herrmann, A.; Buettner, R.;

Jove, R. Nat Rev Cancer. 2014 14(11):736-46, STAT Inhibitors in Cancer, Ed. Alister C. Ward, Humana Press, 2016).

The sensitivity of many cancer cell lines to STAT3 inhibition indicates an oncogene signaling dependence.

Inflammation and immunity are also important parts of cancer etiology. Cancer cells can promote inflammation in the tumor microenvironment and avoid the innate immune system. STAT3 signaling plays an important dual role in this process. STAT3 is activated by pro-inflammatory cytokine signaling and STAT3 activation opposes T-helper cell anti-tumor responses. Ablation of STAT3 signaling leads to a potent immunological antitumor response. STAT3 is more activated in tumor infiltrating immune cells than in normal tissue and targeting STAT3 causes therapeutic antitumor immunity.

In summary, aberrant and deregulated STAT3 promotes cell proliferation and cell survival in both solid and hematological tumors, including breast, lung, brain, colon, prostate, lymphoma and leukemia. Direct inhibitors of STAT3 or inhibitors of STAT3 signaling are thus deemed to be able to mitigate or cure those pathological states.

The treatments for prevention, revocation or reduction of diseases like e.g. cancer are in many ways insufficient. Hence, compounds effective in modulating or inhibiting the above described STAT3 signaling would be desired.

The direct inhibition of STAT3 can be achieved by inhibiting the protein-protein interaction involved in STAT3 dimerization (STAT3 is a dimer of two proteins) or by blocking the protein-DNA interaction required for STAT3 binding to DNA for the initiation of transcription. Alternatively, the production (biosynthesis) of STAT3 can be blocked.

The alternative to direct STAT3 inhibition is to inhibit upstream molecules in the signaling cascade responsible for STAT3 activation (e.g. the JAK kinases). The drawback with this approach is that there are multiple ways to activate STAT3.

The STAT3 SH2 has been targeted with peptidomimetics and non-peptide small molecules (e.g. S3I-M2001) to block STAT3-STAT3 dimerization and DNA binding has been blocked with oligodeoxynucleotide decoys while the production of STAT3 has been inhibited by antisense.

Transcription factors such as STAT3 that are dysregulated in cancer and other illnesses are important targets for potential drugs but the numerous roles played by other transcription factors in healthy cells makes it important to develop transcription factor blocking drugs with a high degree of selectivity and since many transcription factors have similar activation modes and structural similarities this can be difficult to achieve.

(−)-Galiellalactone is a natural product isolated from wood-inhabiting fungi with submicromolar inhibition of IL-6/STAT3 signaling.

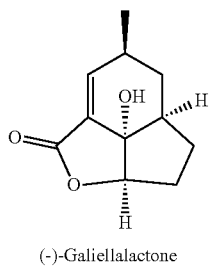

(−)-Galiellalactone

In U.S. Pat. No. 6,512,007 use of galiellalactone as a pharmaceutical for the treatment of e.g. inflammatory processes is disclosed.

The biological effect of (−)-galiellalactone seemingly is due to a direct inhibition of the binding of STAT3-dimers to their regulatory elements (cf. Weidler et al in FEBS Letters 2000, 484, 1-6). Based on this proposed mechanism of action, galiellalactone has been evaluated as an anti-cancer agent. Hellsten et al reported in *Prostate* 68:269-280 (2008) that galiellalactone inhibits the proliferation of STAT3 expressing DU145 prostate cancer cells. Further, Don-Doncow, N.; Escobar, Z.; Johansson, M.; Kjellström, S.; Garcia, V.; Munoz, E.; Sterner, O.; Bjartell, A.; Hellsten, R.; *J. Biol. Chem.* 2014 289(23):15969-78) have shown that galiellalactone binds directly and covalently to STAT3, thus inhibiting the transcriptional activity. Galiellalactone is thus a candidate drug for treatment of cancer. Also Thaper et al ("*GPA500 inhibits the STAT3 activity and suppresses ENZ-resistant Prostate Cancer in vitro*". Daksh Thaper, Sepideh Vahid, Jennifer Bishop, Martin Johansson and Amina Zoubeidi. AACR Annual Meeting 2015, Abstract nr 728) showed that galiellalactone can block STAT3 activity in enzalutamide resistant cells which leads to decreased proliferation and PSA production.

However, galiellalactone shows anti-proliferative and STAT3 inhibitory effects at concentrations that might be difficult to achieve in vivo following oral dosing. Also, low potencies can require doses that lead to unwanted side effects. It would therefore be desirable to develop new compounds based on galiellalactone with retained or preferably improved STAT3 inhibitory potencies while changing the physical-chemical properties allowing for improved drug-like properties in general.

Attempts to modify the activity and properties of galiellalactone have been reported in the art. Nussbaum et al reported in Eur. J. Org. Chem. 2004, 2783-2790 on the modification of individual functional groups of (−)-galiellalactone. Most of the resulting analogues, however, turned out to be completely inactive or much less active than (−)-galiellalactone. Especially, modifications of the conjugated double bond were reported to produce inactive compounds. WO 2012/010555 discloses the preparation and use of tricylic compounds based on a galiellalactone scaffold that inhibit STAT3 and NF-kB signaling.

Further, the physical-chemical properties of galiellalactone and analogues thereof has been addressed by providing pro-drugs thereof (cf. WO 2015/132396). Further, ether analogues of galiellalactone have been reported in WO 2016/193332.

Nevertheless, there remains a need for more potent inhibitors of STAT3 based on galiellalactone.

SUMMARY

The present invention seeks to mitigate, alleviate, circumvent or eliminate at least one, such as one or more, of the above-identified deficiencies by providing a compound, according to an aspect, a compound according to formula (I)

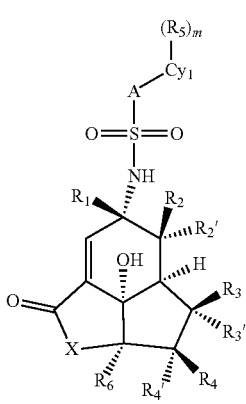

(I)

wherein:

"X" is selected from the group consisting of O, NH, NC1-5 alkylene-aryl, NC1-5 alkylene-heteroaryl, N-aryl, NC1-C3 alkyl, and NC(O)C1-C3 alkyl, wherein said aryl is unsubstituted or substituted with one or several substituents independently selected from the group consisting of C1-C5 alkyl, C1-5 fluoroalkyl, halo, OH, OC1-5 alkyl, C1-5 alkyleneOC1-5 alkyl, cyano, NH, NHC1-5 alkyl, and N(C1-5 alkyl)$_2$, in which the C1-5 alkyl may be the same or different, and nitro, and wherein said heteroaryl is unsubstituted or substituted with one or several substituents independently selected from the group consisting of C1-C5 alkyl, C1-5 fluoroalkyl, halo, oxo, OH, OC1-5 alkyl, C1-5 alkyleneOC1-5 alkyl, cyano, NH, NHC1-5 alkyl, N(C1-5 alkyl)$_2$, in which the C1-5 alkyl may be the same or different, and nitro;

$R_1$ is selected from the group consisting of hydrogen, C1-C5 alkyl, C1-C5 fluoroalkyl, and

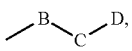

wherein

"B" is C1-C5 alkylene;

"C" is selected from the group consisting —O—, —NH—, —C(O)O—, —OC(O)—, —OSO$_2$—, —NHSO$_2$—, —C(O)NR$_{11}$—, and —N(R$_{11}$)C(O)—, wherein R$_{11}$ is H or C1-C4 alkyl; and "D" is selected from the group consisting of hydrogen, C1-C5 alkyl, C1-C5 fluoroalkyl, and -ECy$_2$, provided that "D" is not hydrogen if "C" is —OSO$_2$— or —NHSO$_2$—, wherein "E" is a direct bond or a C1-C5 alkylene, and Cy$_2$ is aryl or heteroaryl, wherein Cy$_2$ is unsubstituted or substituted with one or several substituents independently selected from the group consisting of C1-5 alkyl, C1-5 fluoroalkyl, halo, OH, OC1-5 alkyl, nitro, cyano, NH, NHC1-5 alkyl, and N(C1-5 alkyl)$_2$, in which the C1-5 alkyl may be the same or different;

$R_2$, $R_2'$, $R_3$, and $R_3'$ are independently selected from the group consisting of H, F, OH, C1-5 alkyl, and C1-5 fluoroalkyl $R_4$ and $R_4'$ are independently selected from the group consisting of H, C1-5 alkyl, halo, and G-Cy$_3$, wherein "G" is a bond or methylene, and Cy$_3$ is aryl or a 5- or 6-membered heteroaryl, wherein Cy$_3$ is unsubstituted or substituted with a one or several substituents independently selected from the group consisting C1-5 alkyl, C1-5 fluoroalkyl, halo, OH, OC1-5 alkyl, C1-5 alkyleneOC1-5 alkyl, nitro, cyano, NH$_2$ and N(C1-5 alkyl)$_2$, in which the C1-5 alkyl may be the same or different;

"A" is independently selected from the group consisting of a bond, C1-5 alkylene, NH, NC1-5 alkyl, C1-3 alkyleneN (R$_{10}$)C1-5 alkylene, and N(R$_{10}$)C1-3 alkylene, wherein R$_{10}$ is H or C1-C4 alkyl;

Cy$_1$ is selected from the group consisting of 5 and 6-membered monocyclic heteroaryls, phenyl, bicyclic heteroaryls, wherein one or both rings are aromatic, naphthyl, 3- to 8-membered non-aromatic heterocycles, and C3-8 non-aromatic carbocycles;

"m" is an integer being 0 (zero), 1, 2, 3, 4, or 5;

$R_5$ is independently selected from the group consisting of C1-8 alkyl, C1-5 fluoroalkyl, halo, cyano, methylene cyano, OH, OC1-5 alkyl, C1-8 alkyleneOH, C1-8 alkyleneOC1-5 alkyl, SH, SC1-5 alkyl, SO$_2$C1-5 alkyl, C1-3 alkyleneSO$_2$C1-5 alkyl, OC1-3 fluroroalkyl, C1-3 alkyleneOC1-3 fluroroalkyl, NH$_2$, NHC1-3 alkyl, N(C1-5 alkyl)$_2$, in which the C1-5 alkyl may be the same or different, C1-3 alkyleneNH$_2$, C1-3 alkyleneNHC1-3 alkyl, C1-3 alkyleneN (C1-5 alkyl)$_2$, in which the C1-5 alkyl may be the same or different, C(O)OH, C(O)OC1-5 alkyl, C1-3 alkyleneC(O) OH, C1-3 alkyleneC(O)OC1-5 alkyl, OC(O)C1-5 alkyl, C1-3 alkyleneOC(O)C1-5 alkyl, NHC(O)C1-3 alkyl, N(C1-3 alkyl)C(O)C1-3 alkyl, C1-3 alkyleneNHC(O)C1-3 alkyl, C1-3 alkyleneN(C1-3 alkyl)C(O)C1-3 alkyl, C(O) NH$_2$, C(O)NHC1-3 alkyl, C(O)N(C1-5 alkyl)$_2$, in which the C1-5 alkyl may be the same or different, C1-3 alkyleneC (O)NH$_2$, C1-3 alkyleneC(O)NHC1-3 alkyl, C1-3 alkyleneC (O)N(C1-5 alkyl)$_2$, in which the C1-5 alkyl may be the same or different, nitro, C(O)C1-C5 alkyl, NHSO$_2$C1-C3 alkyl, N(C1-C3 alkyl)SO$_2$C1-C3 alkyl, NHSO$_2$C1-C3 fluoroalkyl, N(C1-C3 alkyl)SO$_2$C1-C3 fluoroalkyl, OC2-C3alkyleneN (C1-C3 alkyl)$_2$, in which the C1-C3 alkyl may be the same or different, and C3-8 non-aromatic carbocycles;

if Cy$_1$ is a 3- to 8-membered non-aromatic heterocycle or a C3-8 non-aromatic carbocycle and "m" is at least 2, then two R$_5$, being attached to the same carbon atom on said 3- to 8-membered non-aromatic heterocycle or said C3-8 non-aromatic carbocycle, may be connected to each other to form a 3, 4 or 5-membered spiro ring; said spiro ring being a non-aromatic carbocycle or a non-aromatic heterocycle;

if Cy$_1$ is a 3- to 8-membered non-aromatic heterocycle or a C3-8 non-aromatic carbocycle and "m" is at least 2, then two R$_5$, being attached to different atoms in said 3- to 8-membered non-aromatic heterocycle or said C3-8 non-aromatic carbocycle, may be connected to each other to form a bond or C1-5 alkylene bridge; Cy$_1$ thus being a bicyclic residue;

if Cy$_1$ is a monocyclic heteroaryl, a bicyclic heteroaryl, a 3- to 8-membered non-aromatic heterocycle, or a C3-8 non-aromatic carbocycle, then R$_5$ may be a double bonded oxygen (=O), being attached to a carbon or sulfur atom in said heteroaryl or cycle; and $R_6$ is selected from the group consisting of hydrogen and C1-C5 alkyl.

According to another aspect, there is provided a pharmaceutical composition comprising a compound according to formula (I) and at least one pharmaceutically acceptable carrier or excipient. Such a compound and composition is useful in therapy.

According to another aspect, compounds according to formula (I) and compositions comprising such compounds are useful in the treatment of STAT3 signaling related disorders, and especially in the treatment of diseases and disorders selected from the group consisting of: solid cancers, hematological cancers, benign tumors, hyperproliferative diseases, inflammations, autoimmune diseases, graft or transplant rejections, delayed physiological function of grafts or transplants, neurodegenerative diseases and viral infections, such as from solid cancers and hematological cancers.

Further, advantageous features of various embodiments of the invention are defined in the dependent claims and within the detailed description below.

DETAILED DESCRIPTION

Definitions

Unless defined otherwise, all technical and scientific terms used herein have the same meaning as is commonly understood by one of ordinary skill in the art.

In the context of the present application and invention, the following definitions apply:

The term "addition salt" is intended to mean salts formed by the addition of a pharmaceutical acceptable acid, such as organic or inorganic acids, or a pharmaceutical acceptable base. The organic acid may be, but is not limited to, acetic, propanoic, methanesulfonic, benzenesulfonic, lactic, malic, citric, tartaric, succinic or maleic acid. The inorganic acid may be, but is not limited to, hydrochloric, hydrobromic, sulfuric, nitric acid or phosphoric acid. The base may be, but is not limited to, ammonia and hydroxides of alkali or alkaline earth metals. The term "addition salt" also comprises the hydrates and solvent addition forms, such as hydrates and alcoholates.

As used herein, "halo" or "halogen" refers to fluoro, chloro, bromo, and iodo.

As used herein, "alkyl" used alone or as a suffix or prefix, is intended to include both branched and straight chain saturated aliphatic hydrocarbon groups having from 1 to 12 carbon atoms or if a specified number of carbon atoms is provided then that specific number is intended. For example, "C1-6 alkyl" denotes alkyl having 1, 2, 3, 4, 5 or 6 carbon atoms. Examples of alkyl include, but are not limited to, methyl, ethyl, n-propyl, i-propyl, n-butyl, i-butyl, sec-butyl, t-butyl, pentyl, and hexyl.

As used herein, "alkylenyl" or "alkylene" used alone or as a suffix or prefix, is intended to include straight chain saturated aliphatic hydrocarbon groups having from 1 to 12 carbon atoms or if a specified number of carbon atoms is provided then that specific number is intended. For example, "C1-6 alkylenyl" or "C1-6 alkylene" denotes alkylenyl or alkylene having 1, 2, 3, 4, 5 or 6 carbon atoms. As used herein, the groups linked by an alkylene or alkylenyl group are preferably intended to be attached to the first and to the last carbon of the alkylene or alkylenyl-group. In the case of methylene, the first and the last carbon is the same. For example, "H$_2$N(C2 alkylene)NH$_2$", "H$_2$N(C3 alkylene)NH$_2$", "N(C4 alkylene)", "N(C5 alkylene)" and "N(C2 alkylene)$_2$NH" are equivalent to 1,2-diamino ethane, 1,3-diamino propane, pyrrolidinyl, piperidinyl and piperazinyl, respectively. The combination "N(C4-5 alkylene)" refers to pyrrolidinyl and piperidinyl. Examples of alkylene or alkylenyl include, but are not limited to, methylene (—CH$_2$—), ethylene (—CH$_2$CH$_2$—), propylene (—CH$_2$CH$_2$CH$_2$—), and butylene (—CH$_2$CH$_2$CH$_2$CH$_2$—).

As used herein, "alkoxy" or "alkyloxy" is intended to mean an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

As used herein, "fluoroalkyl", "fluoroalkylene" and "fluoroalkoxy", used alone or as a suffix or prefix, refers to groups in which one, two, or three of the hydrogen(s) attached to any of the carbons of the corresponding alkyl, alkylene and alkoxy-groups are replaced by fluoro.

Examples of fluoroalkyl include, but are not limited to, trifluoromethyl, difluoromethyl, fluoromethyl, 2,2,2-trifluoroethyl, 2-fluoroethyl and 3-fluoropropyl.

Examples of fluoroalkylene include, but are not limited to, difluoromethylene, fluoromethylene, 2,2-difluorobutylene and 2,2,3-trifluorobutylene.

Examples of fluoroalkoxy include, but are not limited to, trifluoromethoxy, 2,2,2-trifluoroethoxy, 3,3,3-trifluoropropoxy and 2,2-difluoropropoxy.

As used herein, "non-aromatic carbocycle", whether alone or as a suffix or prefix, is intended to mean non-aromatic saturated and unsaturated carbomonocycles, having from 3 to 8 ring carbon atoms, such as cyclopropanyl, cyclopentanyl, cyclohexanyl, cyclopentenyl and cyclohexenyl. If a prefix, such as C3-C6, is given, when said carbocycle comprises the indicated number of carbon atoms, eg. 3, 4, 5, or 6 carbon atoms. Accordingly, "C6 non-aromatic carbocycle" for example includes cyclohexyl and cyclohexenyl. Non-aromatic unsaturated carbocycles are to be distinguished from aryls, as aryl refers to aromatic ring structures, comprising at least one aromatic ring.

As used herein, "cycloalkyl", whether alone or as a suffix or prefix, is intended to mean a saturated carbomonocycle, having from 3 to 8 ring carbon atoms, such as cyclopropanyl, cyclopentanyl and cyclohexanyl. If a prefix, such as C3-C6, is given, when said cycloalkyl comprises the indicated number of carbon atoms, e.g. 3, 4, 5 or 6 carbon atoms. Accordingly, C6 cycloalkyl corresponds to cyclohexyl.

As used herein, "cycloalkenyl", whether alone or as a suffix or prefix, is intended to mean a monounsaturated carbomonocycle, having from 4 to 8 ring carbon atoms, such as cyclopentenyl and cyclohexenyl. If a prefix, such as C3-C6, is given, when said cycloalkenyl comprises the indicated number of carbon atoms, eg. 3, 4, 5, or 6 carbon atoms. Accordingly, C6 cycloalkenyl corresponds to cyclohexenyl.

As used herein, the term "substitutable" refers to an atom to which hydrogen may be covalently attached, and to which another substituent may be present instead of the hydrogen. A non-limiting example of substitutable atoms includes the carbon-atoms of pyridine. The nitrogen-atom of pyridine is not substitutable according to this definition. Further, according to the same definition, the imine nitrogen at position 3 in imidazole is not substitutable, while the amine nitrogen at position 1 is.

As used herein, the term "aryl" refers to a ring structure, comprising at least one aromatic ring, made up of from 5 to 14 carbon atoms. Ring structures containing 5, 6, or 7 carbon atoms would be single-ring aromatic groups, for example phenyl. Ring structures containing 8, 9, 10, 11, 12, 13, or 14 carbon atoms would be polycyclic, for example naphthyl. The aromatic ring may be substituted at one or more ring positions. The term "aryl" also includes polycyclic ring systems having two or more cyclic rings in which two or more carbons are common to two adjoining rings (the rings are "fused rings") wherein at least one of the rings is aromatic, for example, the other cyclic ring(s) may be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, "heteroaryl" or "hetaryl" refers to an aromatic heterocycle, having at least one ring with aromatic character, (e.g. 6 delocalized electrons) or at least two conjugated rings with aromatic character, (e.g. 4n+2 delocalized electrons where "n" is an integer), and comprising up to about 14 carbon atoms, and having at least one heteroatom ring member such as sulfur, oxygen, or nitrogen in a ring with aromatic character. Heteroaryl or hetaryl groups include monocyclic and bicyclic (e.g., having 2 fused rings) systems. The heteroaryl or hetaryl group may be substituted at one or more ring positions.

Examples of heteroaryl or hetaryl groups include without limitation, pyridyl (i.e., pyridinyl), pyrimidinyl, pyrazinyl, pyridazinyl, triazinyl, furyl (i.e. furanyl), quinolyl, tetrahydroquinolyl, isoquinolyl, tetrahydroisoquinolyl, thienyl, imidazolyl, thiazolyl, indolyl, pyrrolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, benzimidazolyl, indolinyl, and the like.

As used herein, "non-aromatic heterocycle" refers to a monocycle comprising at least one heteroatom ring member, such as sulfur, oxygen, or nitrogen. Such monocyclic rings may be saturated or unsaturated. If unsaturated, the non-aromatic heterocycle may contain one, two or three double bonds or one or two triple bonds. However, non-aromatic heterocycles are to be distinguished from heteroaryl groups.

Examples of non-aromatic heterocycle groups include without limitation azepinyl, dioxolanyl, imidazolinyl, pyrazolidinyl, morpholinyl, piperazinyl, 3H-diazirin-3-yl, oxiranyl, aziridinyl, piperidinyl, piperidinyl-N-oxide, pyrrolidinyl, tetrahydrofuranyl, tetrahydropyranyl, dihydro-2H-pyranyl, tetrahydrothiofuranyl, thiamorpholinyl.

An "oxo" group refers to a "=O" group.

As used herein, the term "relative stereochemistry", such as when e.g. referring to e.g. a drawing of a structure, is relating to the relative spatial arrangement of e.g. substituents or groups of a structure. For example, if the relative stereochemistry is indicated by drawing substituents or groups of a molecule in certain directions, the corresponding mirror image of that molecule will have the same relative stereochemistry. On the other hand, if the "absolute stereochemistry" is indicated by drawing substituents or groups of a molecule in certain directions, a particular enantiomer of that molecule is intended.

Compounds

An embodiment relates to a compound according to formula (I),

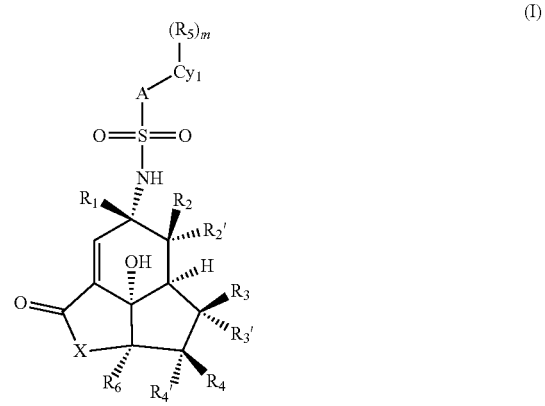

wherein:

"X" is selected from the group consisting of O (oxygen), NH, NC1-5 alkylene-aryl, NC1-5 alkylene-heteroaryl, N-aryl, NC1-C3 alkyl, and NC(O)C1-C3 alkyl, wherein said aryl is unsubstituted or substituted with one or several substituents independently selected from the group consisting of C1-C5 alkyl, C1-5 fluoroalkyl, halo, OH, OC1-5 alkyl, C1-5 alkyleneOC1-5 alkyl, NH, NHC1-5 alkyl, and N(C1-5 alkyl)$_2$, in which the C1-5 alkyl may be the same or different, cyano, and nitro, and wherein said heteroaryl is unsubstituted or substituted with one or several substituents independently selected from the group consisting of C1-C5 alkyl, C1-5 fluoroalkyl, halo, oxo, OH, OC1-5 alkyl, C1-5 alkyleneOC1-5 alkyl, cyano, NH, NHC1-5 alkyl, N(C1-5 alkyl)$_2$, in which the C1-5 alkyl may be the same or different, and nitro;

$R_1$ is selected from the group consisting of hydrogen, C1-C5 alkyl, C1-C5 fluoroalkyl, and

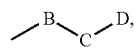

wherein

"B" is C1-C5 alkylene;

"C" is selected from the group consisting —O—, —NH—, —C(O)O—, —OC(O)—, —OSO$_2$—, —NHSO$_2$—, —C(O)NR$_{11}$—, and —N(R$_{11}$)C(O)—, wherein R$_{11}$ is H or C1-C4 alkyl; and "D" is selected from the group consisting of hydrogen, C1-C5 alkyl, C1-C5 fluoroalkyl, and -ECy$_2$, provided that "D" is not hydrogen if "C" is —OSO$_2$— or —NHSO$_2$—, wherein "E" is a direct bond or a C1-C5 alkylene, and Cy$_2$ is aryl or heteroaryl, wherein Cy$_2$ is unsubstituted or substituted with one or several substituents independently selected from the group consisting of C1-5 alkyl, C1-5 fluoroalkyl, halo, OH, OC1-5 alkyl, nitro, cyano, NH, NHC1-5 alkyl, and N(C1-5 alkyl)$_2$, in which the C1-5 alkyl may be the same or different;

$R_2$, $R_2$', $R_3$, and $R_3$' are independently selected from the group consisting of H, F, OH, C1-5 alkyl, and C1-5 fluoroalkyl $R_4$ and $R_4$' are independently selected from the group consisting of H, C1-5 alkyl, halo, and G-Cy$_3$, wherein "G" is a bond or C1-3alkylene, e.g. methylene, and Cy$_3$ is aryl, e.g. phenyl, or a 5- or 6-membered heteroaryl, wherein Cy$_3$ is unsubstituted or substituted with a one or several substituents independently selected from the group consisting C1-5 alkyl, C1-5 fluoroalkyl, halo, OH, OC1-5 alkyl, C1-5 alkyleneOC1-5 alkyl, nitro, cyano, $NH_2$ and $N(C1-5\ alkyl)_2$, in which the C1-5 alkyl may be the same or different;

"A" is independently selected from the group consisting of a bond, C1-5 alkylene, NH, NC1-5 alkyl, C1-3 alkyleneN ($R_{10}$)C1-5 alkylene, and $N(R_{10})$C1-3 alkylene, wherein $R_{10}$ is H or C1-C4 alkyl;

$Cy_1$ is selected from the group consisting of 5 and 6-membered monocyclic heteroaryls, phenyl, bicyclic heteroaryls, wherein one or both rings are aromatic, naphthyl, 3- to 8-membered non-aromatic heterocycles, and C3-8 non-aromatic carbocycles;

"m" is an integer being 0 (zero), 1, 2, 3, 4, or 5;

$R_5$ is independently selected from the group consisting of C1-8 alkyl, C1-5 fluoroalkyl, halo, cyano, methylene cyano, OH, OC1-5 alkyl, C1-8 alkyleneOH, C1-8 alkyleneOC1-5 alkyl, SH, SC1-5 alkyl, $SO_2$C1-5 alkyl, C1-3 alkylene$SO_2$C1-5 alkyl, OC1-3 fluroalkyl, C1-3 alkyleneOC1-3 fluroalkyl, $NH_2$, NHC1-3 alkyl, $N(C1-5\ alkyl)_2$, in which the C1-5 alkyl may be the same or different, C1-3 alkylene$NH_2$, C1-3 alkyleneNHC1-3 alkyl, C1-3 alkyleneN(C1-5 alkyl)$_2$, in which the C1-5 alkyl may be the same or different, C(O)OH, C(O)OC1-5 alkyl, C1-3 alkyleneC(O)OH, C1-3 alkyleneC(O)OC1-5 alkyl, OC(O)C1-5 alkyl, C1-3 alkyleneOC(O)C1-5 alkyl, NHC(O)C1-3 alkyl, N(C1-3 alkyl)C(O)C1-3 alkyl, C1-3 alkyleneNHC(O)C1-3 alkyl, C1-3 alkyleneN(C1-3 alkyl)C(O)C1-3 alkyl, C(O)$NH_2$, C(O)NHC1-3 alkyl, C(O)N(C1-5 alkyl)$_2$, in which the C1-5 alkyl may be the same or different, C1-3 alkyleneC(O)$NH_2$, C1-3 alkyleneC(O)NHC1-3 alkyl, C1-3 alkyleneC(O)N(C1-5 alkyl)$_2$, in which the C1-5 alkyl may be the same or different, nitro, C(O)C1-C5 alkyl, $NHSO_2$C1-C3 alkyl, N(C1-C3 alkyl)$SO_2$C1-C3 alkyl, $NHSO_2$C1-C3 fluoroalkyl, N(C1-C3 alkyl)$SO_2$C1-C3 fluoroalkyl, OC2-C3alkyleneN(C1-C3 alkyl)$_2$, in which the C1-3 alkyl may be the same or different, and C3-8 non-aromatic carbocycles;

if $Cy_1$ is a 3- to 8-membered non-aromatic heterocycle or a C3-8 non-aromatic carbocycle and "m" is at least 2, then two $R_5$, being attached to the same carbon atom on said 3- to 8-membered non-aromatic heterocycle or said C3-8 non-aromatic carbocycle, may be connected to each other to form a 3, 4 or 5-membered spiro ring; said spiro ring being a non-aromatic carbocycle or a non-aromatic heterocycle;

if $Cy_1$ is a 3- to 8-membered non-aromatic heterocycle or a C3-8 non-aromatic carbocycle and "m" is at least 2, then two $R_5$, being attached to different atoms in said 3- to 8-membered non-aromatic heterocycle or said C3-8 non-aromatic carbocycle, may be connected to each other to form a bond or C1-5 alkylene bridge; $Cy_1$ thus being a bicyclic residue;

if $Cy_1$ is a monocyclic heteroaryl, a bicyclic heteroaryl, a 3- to 8-membered non-aromatic heterocycle, or a C3-8 non-aromatic carbocycle, then $R_5$ may be a double bonded oxygen (=O), being attached to a carbon or sulfur atom in said heteroaryl or cycle; and $R_6$ is selected from the group consisting of hydrogen and C1-C5 alkyl.

The compound may be provided in various form, such as a prodrug, free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two hetero-atoms and/or the corresponding tautomeric form resulting from a keto-enol tautomerization. Further, one or more of the atoms in the compound according to formula (I) may be replaced with a corresponding isotope, e.g. hydrogen may be replaced by deuterium or tritium, carbon-12 may be replaced with carbon-13 or -14, etc, as recognized by the skilled person.

According to an embodiment, the compound according to formula (I) is provided as essentially pure enantiomer. If provided as an essentially pure enantiomer, the compound according to formula (I) may have an enantiomeric excess of at least 95%, such as at least 98 or even 99%.

Further, the compound according to formula (I) may be provided as a pro-drug. As an example, a thiol may be used to convert compounds according to formula (I) into a pro-drug as disclosed in WO 2015/132396.

Introducing a sulfonamide geminally to the methyl group in galiellalactone was found to alter its physical-chemical properties, while maintaining or even improving its potency, provided that the sulfonamide has a cyclic substituent.

In galiellalactone a methyl group is present in the 4 position (cf. $R_1$). According to an embodiment, $R_1$ is thus methyl. However, according to a preferred selection $R_1$ may also be independently selected from the group consisting of hydrogen, methyl, C1fluoroalkyl, and

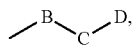

wherein

B is —$CH_2$— (methylene);

C is selected from the group consisting —O—, —NH—, —C(O)O—, —OC(O)—, —$NHSO_2$—, —C(O)$NR_{11}$—, and —$N(R_{11})$C(O)—, wherein $R_{11}$ is H or C1-C3 alkyl; and D is selected from the group consisting of hydrogen, C1-C3 alkyl, C1-C3 fluoroalkyl, provided that "D" is not hydrogen if "C" is —$NHSO_2$—, and -E$Cy_2$, wherein E is a direct bond or a methylene, and $Cy_2$ is aryl or heteroaryl, wherein $Cy_2$ is unsubstituted or substituted with one or several substituents independently selected from the group consisting of methyl, C1 fluoroalkyl, halo, OH, OC1-5 alkyl, cyano, $NH_2$, NHC1-5 alkyl, and $N(C1-5\ alkyl)_2$, in which the C1-5 alkyl may be the same or different. Further, $R_1$ may be independently selected from the group consisting of methyl, $CH_2OH$, and $CH_2$OC1-C3 alkyl, e.g. $CH_2$OMe, $CH_2$OEt, $CH_2$OnPr or $CH_2$OiPr. Synthetic methods for modifying the methyl group of galiellalactone are disclosed herein further below.

In galiellalactone no further substituents apart from methyl group and the hydroxyl group are present on the tricyclic scaffold. According to an embodiment, $R_2$, $R_2'$, $R_3$, and $R_3'$ thus all are hydrogen. As disclosed in WO 2012/010555, substituents may be introduced as $R_2$, $R_2'$, $R_3$, and/or $R_3'$, as well as $R_4$ and/or $R_4'$. Though preferred, $R_2$, $R_2'$, $R_3$, and $R_3'$ are not limited to being hydrogen, but may be selected from the group consisting of H, F, OH, C1-5 alkyl, and C1-5 fluoroalkyl, preferably from the group consisting of H, F, and OH. Further, also $R_4$ and $R_4'$ are hydrogen in galiellalactone. According to an embodiment both $R_4$ and $R_4'$ are hydrogen. Further, $R_4$ and $R_4'$ may be independently selected from the group consisting of H, methyl, and G-$Cy_3$, wherein "G" is a bond or —$CH_2$— (methylene), and $Cy_3$ is an unsubstituted aryl.

Galiellalactone is a lactone, however as recognized by the skilled person, lactams are closely related to lactones, though being more hydrolytically stable. Compounds according to formula (I) may thus be lactones, "X" being O (oxygen), as well as lactams, e.g. "X" being NH, NC1-5 alkylene-aryl, e.g. $NCH_2$-aryl, NC1-5 alkylene-heteroaryl, N-aryl, or NC1-C3 alkyl. Further, X may be NC(O)C1-C3 alkyl. The aryl in NC1-5 alkylene-aryl and N-aryl, respectively, may be unsubstituted or substituted with one or several substituents independently selected from the group consisting of C1-C5 alkyl, C1-5 fluoroalkyl, halo, OH, OC1-5 alkyl, C1-5 alkyleneOC1-5 alkyl, cyano, NH, NHC1-5 alkyl, N(C1-5 alkyl)$_2$, in which the C1-5 alkyl may be the same or different, and nitro. Similarly, the heteroaryl in NC1-5 alkylene-heteroaryl may be unsubstituted or substituted with one or several substituents independently selected from the group consisting of C1-C5 alkyl, C1-5 fluoroalkyl, halo, oxo (i.e. the heteroaryl comprising a carbonyl group), OH, OC1-5 alkyl, C1-5 alkyleneOC1-5 alkyl, cyano, NH, NHC1-5 alkyl, N(C1-5 alkyl)$_2$, in which the C1-5 alkyl may be the same or different, and nitro. The heteroaryl is preferably a monocyclic 5- or 6-membered heteroaryl. While the length of the alkylene linker in NC1-5 alkylene-aryl and NC1-5 alkylene-heteroaryl, respectively, may vary, the alkylene linker is preferably methylene. Further, the aryl in NC1-5 alkylene-aryl is preferably phenyl. If the phenyl is substituted, the phenyl is preferably mono-substituted in the para-position.

According to an embodiment, "X" is selected from the group consisting of O and NCH$_2$-phenyl. The phenyl in NCH$_2$-phenyl may be unsubstituted or substituted with one or several substituents independently selected from the group consisting of methyl, CF$_3$, halo, OH, OMe, CH$_2$OCMe, cyano, NH, NHMethyl, and N(Methyl)$_2$, and nitro. Further, the compound according to formula (I) may be a lactone, "X" thus being "O" (oxygen).

In formula "A" represents a linker, linking the cyclic group Cy$_1$ to the sulfonamide group (—NHSO$_2$—). The linker "A" may be independently selected from the group consisting of a bond, i.e. the introduced group in the 4-position is —NHSO$_2$-Cy1-(R$_5$)$_m$, C1-5 alkylene, e.g. methylene, NH, NC1-5 alkyl, C1-3 alkyleneN(R$_{10}$)C1-5 alkylene, and N(R$_{10}$)C1-3 alkylene, wherein R$_{10}$ is H or C1-C4 alkyl. Preferably, the linker "A" is selected from the group consisting of a bond and —CH$_2$— (methylene), i.e. the introduced group in the 4-position is —NHSO$_2$-Cy1-(R$_5$)$_m$ or —NHSO$_2$—CH$_2$-Cy1-(R$_5$)$_m$. With regard to the sulfonamide itself, it was found that substitution of the nitrogen affected the potency negative. Thus, the nitrogen in the sulfonamide is preferably unsubstituted.

As already mentioned the sulfonamide should have a cyclic substituent (cf. Cy1). The cyclic group may be aromatic and well as non-aromatic. Further, the group is not restricted to monocycles, but includes other cycles as well, e.g. bi-cycles. However, aromatic cycles, i.e. aryls, e.g. phenyl, and heteroaryls, e.g. 5-membered heteroaryls, are preferred. According to an embodiment, Cy$_1$ is selected from the group consisting of phenyl, 5-membered heteroaryls, and 6-membered heteroaryls. The 5-membered heteroaryls are preferably selected from the group consisting of furan, thiophene, oxazole, thiazole, isoxazole, and oxadiazole. The 6-membered heteroaryls are preferably selected from the group consisting of, pyridinyl, pyrimidinyl, pyridazinyl, and pyrazinyl. Preferably, Cy$_1$ is selected from the group consisting of phenyl, thiophenyl, furanyl, pyridinyl, pyrimidinyl, pyrazinyl, oxazolyl, isoxazolyl, oxadiazolyl, isothiazolyl, and thiazolyl, such as from phenyl, pyridinyl, and thiophenyl.

The cyclic substituent Cy$_1$ may be unsubstituted, i.e. the integer "m" being 0 (zero) and R$_5$ being absent, or substituted, i.e. the integer "m" being 1 or more and R$_5$ being present. According to an embodiment, the cyclic substituent Cy$_1$ is substituted and the integer "m" is 1, 2, 3, 4, or 5. The number of substituents is typically quite low, thus the integer "m" may be 1, 2, or 3, such as being is 1 or 2.

If present, the substituent R$_5$ is, independently if "m" is 2 or more, selected from the group consisting of C1-8 alkyl, C1-5 fluoroalkyl, halo, cyano, methylene cyano, OH, OC1-5 alkyl, C1-8 alkyleneOH, C1-8 alkyleneOC1-5 alkyl, SH, SC1-5 alkyl, SO$_2$C1-5 alkyl, C1-3 alkyleneSO$_2$C1-5 alkyl, OC1-3 fluroroalkyl, C1-3 alkyleneOC1-3 fluroroalkyl, NH2, NHC1-3 alkyl, N(C1-5 alkyl)2, in which the C1-5 alkyl may be the same or different, C1-3 alkyleneNH2, C1-3 alkyleneNHC1-3 alkyl, C1-3 alkyleneN(C1-5 alkyl)2, in which the C1-5 alkyl may be the same or different, C(O)OH, C(O)OC1-5 alkyl, C1-3 alkyleneC(O)OH, C1-3 alkyleneC(O)OC1-5 alkyl, OC(O)C1-5 alkyl, C1-3 alkyleneOC(O)C1-5 alkyl, NHC(O)C1-3 alkyl, N(C1-3 alkyl)C(O)C1-3 alkyl, C1-3 alkyleneNHC(O)C1-3 alkyl, C1-3 alkyleneN(C1-3 alkyl)C(O)C1-3 alkyl, C(O)NH2, C(O)NHC1-3 alkyl, C(O)N(C1-5 alkyl)2, in which the C1-5 alkyl may be the same or different, C1-3 alkyleneC(O)NH2, C1-3 alkyleneC(O)NHC1-3 alkyl, C1-3 alkyleneC(O)N(C1-5 alkyl)2, in which the C1-5 alkyl may be the same or different, nitro, C(O)C1-C5 alkyl, NHSO$_2$C1-C3 alkyl, N(C1-C3 alkyl)SO$_2$C1-C3 alkyl, NHSO$_2$C1-C3 fluoroalkyl, N(C1-C3 alkyl)SO$_2$C1-C3 fluoroalkyl, OC2-C3alkyleneN(C1-C3 alkyl)$_2$, in which the C1-3 alkyl may be the same or different, and C3-8 non-aromatic carbocycles. Further, if Cy$_1$ is a 3- to 8-membered non-aromatic heterocycle or a C3-8 non-aromatic carbocycle and "m" is at least 2, then two R$_5$, being attached to the same carbon atom on said 3- to 8-membered non-aromatic heterocycle or said C3-8 non-aromatic carbocycle, may be connected to each other to form a 3, 4 or 5-membered spiro ring, the spiro ring being a non-aromatic carbocycle or a non-aromatic heterocycle. Furthermore, if Cy$_1$ is a 3- to 8-membered non-aromatic heterocycle or a C3-8 non-aromatic carbocycle and "m" is at least 2, then two R$_5$, being attached to different atoms in said 3- to 8-membered non-aromatic heterocycle or said C3-8 non-aromatic carbocycle, may be connected to each other to form a bond or C1-5 alkylene bridge, Cy$_1$ thus being a bicyclic residue. In addition if Cy$_1$ is a monocyclic heteroaryl, a bicyclic heteroaryl, a 3- to 8-membered non-aromatic heterocycle or a C3-8 non-aromatic carbocycle, then R$_5$ may be a double bonded oxygen (═O), being attached to a carbon or sulfur atom in said heteroaryl or cycle.

Preferably, R$_5$ is a not large substituent. Thus, R$_5$ may be selected from the group consisting of methyl, C1 fluoroalkyl, e.g. —CF$_3$ or —CHF$_2$, halo, cyano, OH, -OMe, C1-2 alkyleneOH, e.g. CH$_2$OH, SO$_2$C1-3 alkyl, OC1 flurroroalkyl, NH$_2$, NHC1-3 alkyl, N(C1-3 alkyl)$_2$, in which the C1-3 alkyl may be the same or different, e.g. NMe$_2$, C(O)OH, C(O)OC1-3 alkyl, e.g. C(O)OMe, NHC(O)C1-3 alkyl, e.g. NHC(O)Me, N(C1-3 alkyl)C(O)C1-3 alkyl, C(O)NH$_2$, C(O)NHC1-3 alkyl, C(O)N(C1-3 alkyl)$_2$, in which the C1-3 alkyl may be the same or different, e.g. C(O)NMe$_2$, C(O)C1-C3 alkyl, e.g. C(O)Me, NHSO$_2$C1-C3 alkyl, N(C1-C3 alkyl)SO$_2$C1-C3 alkyl, OC2-C3alkyleneN(C1-C3 alkyl)$_2$, in which the C1-3 alkyl may be the same or different, and C3-8 non-aromatic carbocycles. More preferred R$_5$ is selected from the group consisting of methyl, —NH$_2$, fluorine, —CF$_3$, —CHF$_2$, bromine and chlorine.

In galiellalactone, the tertiary carbon next to the lactone or lactam is unsubstituted (i.e. R$_6$ is hydrogen). However, it was found that this tertiary carbon actually also may be substituted by addition of a suitable Grignard reagent to an oxo-derivative of galiellalactone followed by lactonization as outlined further below. Thus, R$_6$ may as well be a C1-C5 alkyl, such as methyl. R$_6$ is preferably hydrogen or methyl;

and more preferably hydrogen. It was found that compounds in which $R_6$ is C1-C5 alkyl have improved stability in aqueous media.
Specific examples of preferred compounds, comprises compounds selected from the group consisting of:
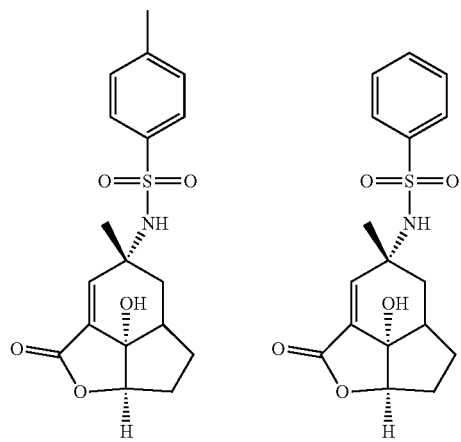
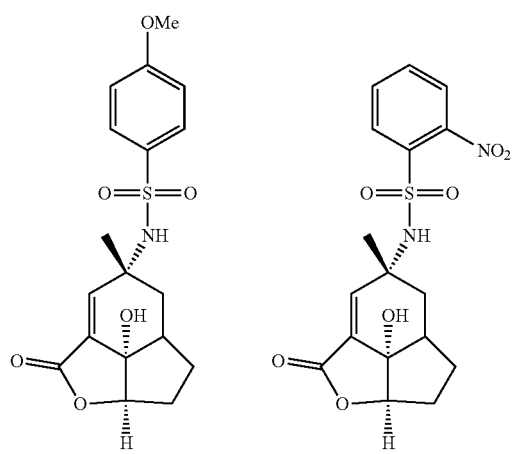
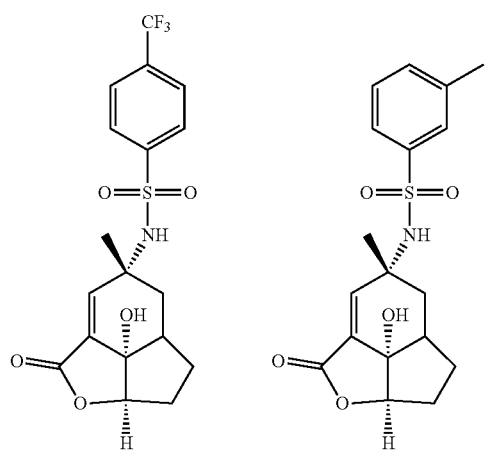
-continued
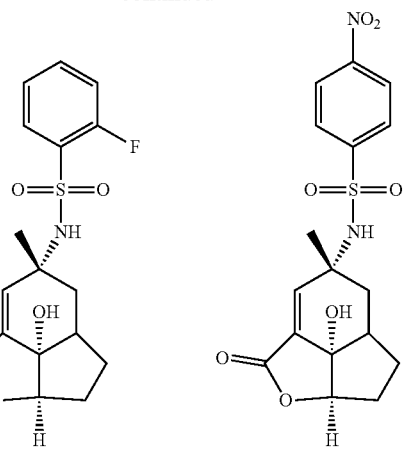
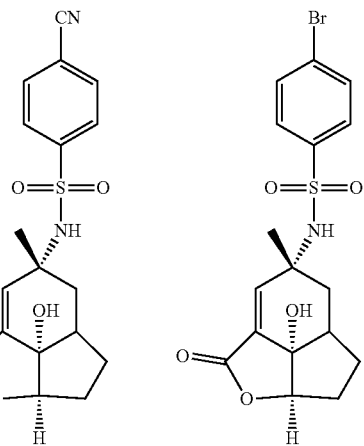
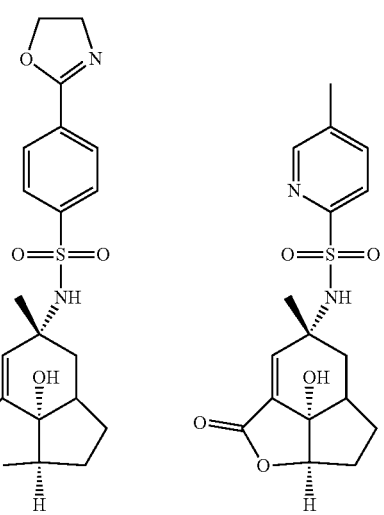

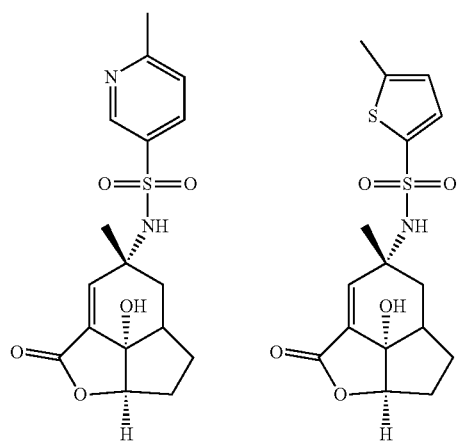
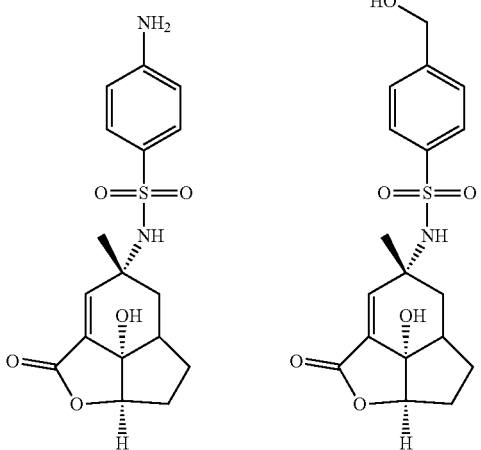
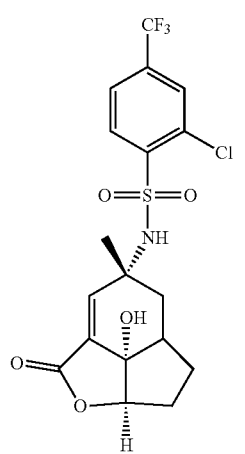
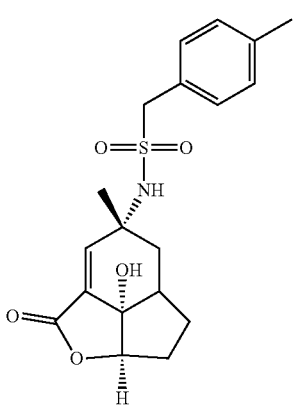
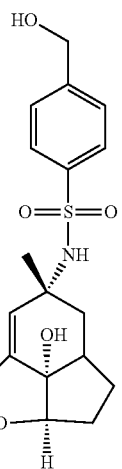
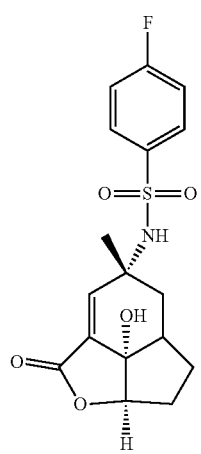
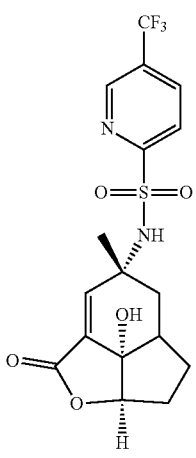
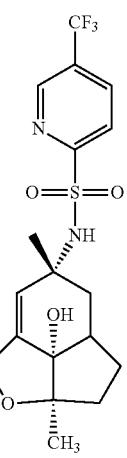

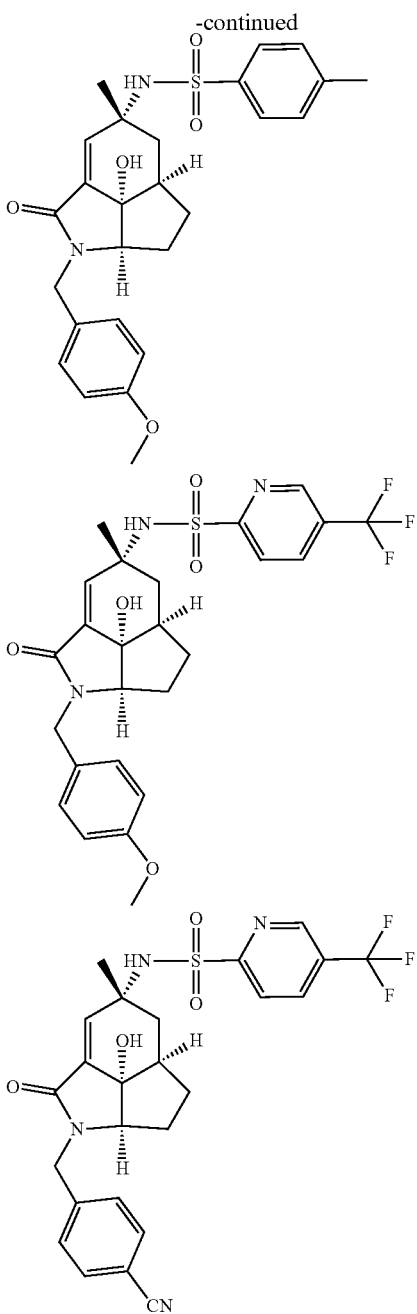

Pharmaceutical Compositions

Compounds disclosed herein, e.g. compounds according to formula (I), or preferred selections thereof, may be formulated into conventional pharmaceutical compositions, e.g. medicaments. According to an embodiment, there is thus provided a pharmaceutical composition comprising a compound as disclosed herein and at least one pharmaceutically acceptable carrier or excipient.

In this context "pharmaceutically acceptable" is intended to mean an excipient or carrier that, at the dosage and concentrations employed, does not cause any unwanted effects in the patients to whom it is administered. Such pharmaceutically acceptable carriers and excipients are well-known in the art. Further, pharmaceutical composition as described herein, may also comprise pharmaceutically diluents, stabilizers and the like.

The pharmaceutically acceptable carriers may be either solid or liquid.

Pharmaceutical compositions may typically be provided either as solid or as liquid preparations.

Solid form preparations include, but are not limited to, powders, tablets, dispersible granules, capsules, cachets, and suppositories. Powders, tablets, dispersible granules, capsules, cachets may be used as solid dosage forms suitable for oral administration, while suppositories may be used for rectal administration.

A solid carrier may be one or more substances, which may also act as diluent, flavoring agent, solubilizer, lubricant, suspending agent, binder, or tablet disintegrating agent. A solid carrier may also be an encapsulating material. Suitable carriers include, but are not limited to, magnesium carbonate, magnesium stearate, talc, lactose, sugar, pectin, dextrin, starch, tragacanth, methylcellulose, sodium carboxymethyl cellulose, low-melting wax, cocoa butter, and the like.

In powders, the carrier is normally a finely divided solid, which is in a mixture with the compound as disclosed herein, also typically being finely divided. In tablets, the active component may be mixed with the carrier having the necessary binding properties in suitable proportions and compacted in the shape and size desired.

For preparing suppository compositions, a low-melting wax, such as a mixture of fatty acid glycerides and cocoa butter, may first be melted and the active ingredient, like a compound of the invention, may then be dispersed therein by, for example, stirring. The molten homogeneous mixture may then be poured into convenient sized molds and allowed to cool and solidify.

The term composition is also intended to include the formulation of the active component with encapsulating material as a carrier providing a capsule in which the active component (with or without other carriers) is surrounded by a carrier which is thus in association with it. Similarly, cachets are included.

Liquid form preparations include, but are not limited to, solutions, suspensions, and emulsions. For example, dissolvation or dispersion of the compounds disclosed herein in sterile water or mixture of water and propylene glycol may provide liquid preparations suitable for parenteral administration. Liquid compositions may also be formulated in solution in aqueous polyethylene glycol solution.

Aqueous solutions for oral administration may be prepared by dissolving the active component, like a compound of the invention, in water and adding suitable colorants, flavoring agents, stabilizers, and thickening agents as desired. Aqueous suspensions for oral use may be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

A pharmaceutical composition according to embodiments disclosed herein may be administered through different routes such as, but not limited to, intravenously, intraperitoneally, intramuscularly, intranasally, subcutaneously, sublingually, rectally, orally as well as through inhalation or insufflation.

Depending on the mode of administration, the pharmaceutical composition may include from about 0.05 wt % (percent by weight) to about 99 wt %, such as about 0.10 wt % to about 50 wt %, about 0.5 wt % to about 30, or about 1.0 wt % to about 25 wt %, of a compound disclosed herein, all percentages by weight being based on the total weight of the composition.

Therapy

Compounds disclosed herein, e.g. compounds according to formula (I), or preferred selections thereof, as well as pharmaceutical compositions comprising such a compound, may be used in therapy.

Compounds disclosed herein, e.g. compounds according to formula (I), or preferred selections thereof, as well as pharmaceutical compositions comprising such compounds, may be used for the treatment of various diseases or conditions in humans or mammals, such as dogs, cats, horses, cows or other mammals; in particular domestic mammals. Mammals may be treated for the same diseases and conditions as humans may be treated for.

When used in therapy, a pharmaceutical composition according to embodiments herein may be administered to the patient in a pharmaceutically effective dose. By "pharmaceutically effective dose" is meant a dose that is sufficient to produce the desired effects in relation to the condition for which it is administered. The exact dose may be dependent on the activity of the compound, manner of administration, nature and severity of the disorder and/or disease and the general conditions, such as age and body weight of the patient.

A therapeutically effective amount for the practice of the present invention may be determined by one of ordinary skill in the art using known criteria including the age, weight and response of the individual patient, and interpreted within the context of the disease which is being treated or which is being prevented.

Treatment of STAT3 Signaling Related Disorder, Inhibition of Cancer Cell Proliferation and Inhibition of Cancer Related Immunosuppressive Mechanisms The parent compound galiellalactone and related compounds (cf. WO 2012/010555 and WO 2016/193332) are deemed to be covalent inhibitors of STAT3, binding directly to STAT3 and preventing DNA binding. As described herein above, the transcription factor STAT3 has emerged as a highly promising target for the treatment of various cancers, e.g. castration resistant prostate cancer (CRPC). In CRPC, constitutive activation of STAT3 is implicated in drug resistance, the progression of androgen independent growth, metastasis, immune avoidance and tumor growth.

Galiellalactone has indeed been found to inhibit proliferation of DU145 prostate cancer cells (cf. Hellsten et al; *Prostate* 68; 269-280, 2008). Without being bound to any theory, it is believed that galiellalactone induces apoptosis by down regulating STAT3 related genes. Galiellalactone also inhibits immunosuppressive cells that play a role in cancer, e.g. prostate cancer. It was shown that galiellalactone is able to inhibit the DU145 and LNCaP-IL6+ prostate cancer cell line induction of a monocyte population displaying MDSC markers ("Prostate cancer cell-induced differentiation of human monocytes into MDSCs ex vivo is inhibited by targeting STAT3 ("*GPA*500 *inhibits the STAT3 activity and suppresses ENZ-resistant Prostate Cancer in vitro*". Rebecka Hellsten, Karin Leandersson, Anders Bjartell and Martin H. Johansson).

The present compounds were found to be equally or more potent as STAT3 inhibitors than galiellalactone (cf. experimental). Further, they do have other favorable physical-chemical and drug-like properties. They may thus be used in the treatment or prevention of a STAT3 signaling related disorder. Especially, the present compounds may be used in the treatment of cancer, as they inhibit proliferation of cancer cells and block the immunosuppressive function of immune cells that may be present in the tumor microenvironment An embodiment thus relates to compounds and pharmaceutical compositions disclosed herein, e.g. compounds according to formula (I), or preferred selections thereof, for use in treatment or prevention of a STAT3 signaling related disorder. Examples of STAT3 signaling related disorders include various cancers, such as solid cancers and hematological cancer, benign tumors, hyperproliferative diseases, inflammation, autoimmune diseases, graft or transplant rejections, delayed physiological function of grafts or transplants, neurodegenerative diseases or viral infections, such as from solid cancers and hematological cancers.

According to an embodiment, a preferred selection of compounds according to formula (I), are compounds according to formula (I) having greater potency than galiellalactone in inhibiting the activity of the STAT3 transcription factor.

In addition to the effect on STAT3, galiellalactone has also been shown to block TGF-beta signaling (Rudolph et al Cytokine. 2013 January; 61(1):285-96) and to be effective in an in vivo murine model of allergic asthma (Hausding et al Int Immunol. 2011 January; 23(1):1-15).

Regardless of their interference with STAT3 signaling or not, compounds and pharmaceutical compositions disclosed herein may be used in the treatment or prevention of cancer. Another embodiment thus relates to compounds and pharmaceutical compositions disclosed herein for use in the prevention or treatment of cancer, such as solid cancers or hematological cancers.

Examples of solid cancers include, but are not limited to, sarcomas, breast cancer, prostate cancer, head and neck cancer, brain tumors, colorectal cancer, lung cancer, pancreatic cancer, cervical cancer, ovarian cancer, melanoma, gastric cancers, renal cell carcinoma, endometrial cancer, sarcomas and hepatocellular carcinomas. Examples hematological cancers include, but are not limited to, chronic myelogenous leukemia, acute myelogenous leukemia, cutaneous T-cell lymphoma, Hodgkin's disease, anaplastic large-cell lymphoma and Burkitt's lymphoma.

Further, the cancers to be treated by compounds and pharmaceutical compositions disclosed herein, are according to an embodiment selected from the group consisting of leukemia, lymphomas, multiple myeloma, breast cancer, prostate carcinoma, lung cancer (non-small-cell), renal cell carcinoma lung cancer, hepatocellular carcinoma, cholangiocarcinoma, ovarian carcinoma, pancreatic adenocarcinoma, melanoma, glioblastoma and head and neck squamous cell carcinoma. Furthermore, the cancer to be treated by compounds and pharmaceutical compositions disclosed herein, is according to an embodiment prostate carcinoma.

Regardless of their interference with STAT3 signaling or not, compounds and pharmaceutical compositions disclosed herein may be used in the treatment or prevention of benign tumors. Another embodiment thus relates to compounds and pharmaceutical compositions disclosed herein for use in the prevention or treatment of benign tumors, including for example Cardiac myxoma and Castleman's disease.

Compounds and pharmaceutical compositions disclosed herein may inhibit proliferation or angiogenesis, induces apoptosis, sensitizes to apoptosis or causes cytotoxicity of cancer cells, including cancer stem cells e.g. leukemic, prostate and breast cancer stem cells. Preferably, the cancer displays elevated or aberrant STAT3 signaling or activity, constitutively phosphorylated or active STAT3 or increased STAT3 protein expression. According to an embodiment, compounds and pharmaceutical compositions disclosed herein are thus used to inhibit the growth or migration of cells. These cells may have elevated or aberrant STAT3 signaling or activity, constitutively phosphorylated or active STAT3 or increased STAT3 protein expression. Hence, associated diseases and disorders, such as hyperproliferative diseases, may be treated or prevented by use of compounds and pharmaceutical compositions disclosed herein. Another embodiment thus relates to compounds and pharmaceutical compositions disclosed herein for use in the prevention or treatment hyperproliferative diseases.

IL-6 often is often involved in STAT3 signaling. Independently of involving effects or not of STAT3 signaling, compounds and pharmaceutical compositions disclosed herein may be used for treatment or prevention of IL-6 mediated inflammation and/or autoimmune diseases and disorders, such as diseases and disorders related to the production of acute phase proteins. Another embodiment thus relates to compounds and pharmaceutical compositions disclosed herein for use in the prevention or treatment of IL-6 mediated inflammation and/or autoimmune diseases and disorders. Such diseases and disorders include, but are not limited to, atherosclerosis, diabetes type 2, dementia, osteoporosis, hypertension, coronary artery disease, obesity.

According to an embodiment, compounds and pharmaceutical compositions disclosed herein are used for the prevention or treatment of inflammatory and/or autoimmune diseases including, but not limited to, arthritis, Crohn's disease, ulcerative colitis, rheumatoid arthritis, inflammatory bowel diseases, asthma, allergy, e.g. Atopic dermatitis, systemic lupus erythematosus, uveitis and COPD. In addition, compounds of the invention may be used for the suppression of graft and transplant rejection, or for improved onset of the physiological functions of such grafts and transplants after transplantation.

According to an embodiment, compounds and pharmaceutical compositions disclosed herein are used for the prevention or treatment of inflammatory, autoimmune and neurodegenerative diseases affecting the CNS including, but not limited to, Parkinson's disease, Alzheimer's disease, multiple sclerosis, stroke and ischemia reperfusion injury.

According to an embodiment, compounds and pharmaceutical compositions disclosed herein are used for the prevention or treatment of chronic viral infections including, but not limited to, hepatitis C, herpes, infections caused by Kaposis Sarcoma-associated herpes virus (KSHV) and Epstein-Barr virus related infections.

According to an embodiment, compounds and pharmaceutical compositions disclosed herein are prevention or treatment of hyperproliferative diseases including, but not limited to, psoriasis.

When used in therapy, a pharmaceutical composition according embodiments herein may be administered to the patient in a pharmaceutically effective dose. By "pharmaceutically effective dose" is meant a dose that is sufficient to produce the desired effects in relation to the condition for which it is administered. The dose required for the therapeutic or preventive treatment of a particular disease or disorder will necessarily be varied depending on the host treated, the route of administration and the severity of the illness being treated. Further, the exact dose may be dependent on the activity of the compound, manner of administration, nature and severity of the disorder and/or disease and the general conditions, such as age and body weight of the patient.

A therapeutically effective amount for the practice of the present invention may be determined by one of ordinary skill in the art using known criteria including the age, weight and response of the individual patient, and interpreted within the context of the disease which is being treated or which is being prevented.

Evidently, compounds and pharmaceutical compositions disclosed herein may be used for the manufacture of a medicament for use in such treatment and prevention as disclosed herein.

Similarly, compounds and compositions disclosed herein may obviously also be used in method for treating or preventing such diseases and disorders as have been disclosed herein. Such a method includes the step of administering an effective amount of the compound, or the pharmaceutical composition, to a subject in need for such treatment.

In the context of the present specification, the term "therapy" and "treatment" includes prevention or prophylaxis, unless there are specific indications to the contrary. The terms "therapeutic" and "therapeutically" should be construed accordingly.

According to an embodiment, treatment does also encompass pre-treatment, i.e. prophylactic treatment.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

Combination Therapy

As already described, pharmaceutical composition as disclosed herein may be used in therapy, the disclosed compounds, e.g. compounds according to formula (I), or preferred selections thereof, acting as the principal therapeutic agent.

However, any of the disclosed compounds may also be supplemented with additional therapeutically active agent(s). According to an embodiment, the present pharmaceutical compositions do comprise one or more additional therapeutic agent(s). Preferably, the one or more additional therapeutic agents are selected among therapeutic agents having a mechanism of action that differ from the mechanism of action of the compound disclosed herein. An advantageous synergistic effect between the therapeutic agent and the compound disclosed herein may then occur, allowing a more effective combat of e.g. a disease than if only such a therapeutic agent or a compound as disclosed herein is used. The additional therapeutic agent may be an anti-cancer agent, e.g. chemotherapeutic agents. Further, also other therapeutic agents well known in the art, being effective for other diseases and conditions as described herein, may advantageously be used in combination with a compound as disclosed herein, in order to e.g. achieve a synergistic effect.

According to an embodiment, a compound or a pharmaceutical composition as disclosed herein is used in combination with other treatments or therapies, in particular cancer therapies, including chemotherapy, immunotherapy, radiation therapy, gene therapy, cell therapy and surgery. As an example, compounds disclosed herein may enhance anti-tumor immune mediated cytotoxicity or reverse resistance. Hence, synergistic effects between a compound disclosed herein, and another treatment or therapy or an immune mediated response, may favorably occur.

According to an embodiment, a pharmaceutical composition according to embodiments herein may be administered alone or in combination with other therapeutic agents. These agents may be incorporated as part of the same pharmaceutical composition or may be administered separately. It is well known in the art that a combination of mechanistically unrelated therapeutic agents in the same medicament may have beneficial effects in the treatment of conditions or diseases characterized by e.g. abnormal immune regulation, abnormal hematopoiesis, inflammation or oncogenesis.

Examples of other therapeutic agents include, but is not limited to, anti-cancer agents such as Abraxane, Abiraterone, Aldesleukin, Alemtuzumab, Aminolevulinic Acid, Anastrozole, Aprepitant, Arsenic Trioxide, Azacitidine, Bendamustine Hydrochloride, Bevacizumab, Bexarotene, Bortezomib, Bleomycin, Cabazitaxel, Capecitabine, Carboplatin, Cetuximab, Cisplatin, Clofarabine, Crizotinib, Cyclophosphamide, Cytarabine, Dacarbazine, Dasatinib, Daunorubicin Hydrochloride, Decitabine, Degarelix, Denileukin Diftitox, Dexrazoxane Hydrochloride, Docetaxel, Doxorubicin Hydrochloride, Doxorubicin Hydrochloride Liposome, Eltrombopag Olamine, Enzalutamide, Epirubicin Hydrochloride, Erlotinib Hydrochloride, Etoposide, Etoposide Phosphate, Everolimus, Exemestane, Filgrastim, Fludarabine Phosphate, Fluorouracil, Fulvestrant, Gefitinib, Gemcitabine Hydrochloride, Ibritumomab Tiuxetan, Imatinib Mesylate, Imiquimod, Irinotecan Hydrochloride, Ixabepilone, Lapatinib Ditosylate, Lenalidomide, Letrozole, Leucovorin Calcium, Leuprolide Acetate, Liposomal Cytarabine, Methotrexate, Nelarabine, Nilotinib, Ofatumumab, Oxaliplatin, Paclitaxel, Palifermin, Palonosetron Hydrochloride, Panitumumab, Pazopanib Hydrochloride, Pegaspargase, Pemetrexed Disodium, Plerixafor, Pralatrexate, Raloxifene Hydrochloride, Rasburicase, Recombinant HPV Bivalent Vaccine, Recombinant HPV Quadrivalent Vaccine, Rituximab, Romidepsin, Romiplostim, Sipuleucel-T, Sorafenib Tosylate, Sunitinib Malate, Talc, Tamoxifen Citrate, Tasquinimod, TAK700, Temozolomide, Temsirolimus, Thalidomide, Topotecan Hydrochloride, Toremifene, Tositumomab and I 131 Iodine Tositumomab, Trastuzumab, Vincristine Sulfate, Vorinostat, ARN-509, ODM-201, custirsen, AT 101, cisplatin, abozantinib, dasatinib, MK2206, axitinib, saracatinib, tivantinib, linsitinib, GSK2636771, BKM120, Vorinostat, panobinostat, azacitidine, IPI-504, STA9090, lenalidomid, OGX-427, Zoledronic Acid and Xofigo, MEDI4736, tremelimumab, ipilimumab, Pembrolizumab, Nivolumab, Durvalumab, Atezolizumab or the like.

When a compound according to embodiments disclosed herein is combined with at least another therapeutic agent, such as an anti-cancer agent, in a pharmaceutical composition, such as a medicament, a therapeutically effective dose of the pharmaceutical composition may comprise 1 to 10 times less than the respective established therapeutically effective dose of a component, i.e. a compound according to the invention or the therapeutic agent, when administered alone for prevention or treatment of the same disease or condition.

Accordingly, by combining a compound according to embodiments disclosed herein with another therapeutic agent, such as an anti-cancer agent, it may be possible to achieve synergistic effects compared to if only a compound according to the present invention, or the other therapeutic agent, were administrated alone.

For example, compounds as disclosed herein, e.g. compounds according to formula (I), may be used for reversing drug resistance, increasing response rates and/or enhancing effects of anti-cancer agents, thus offering the possibility of lowering the dose of the anticancer agent to avoid side-effects and/or enhancing the efficacy and response rate.

Methods of Preparation

Another embodiment of the present invention relates to a process for preparing a compound according to formula (I). Further, additionally embodiments relate to synthetic intermediates, which are useful in the synthesis of a compound of formula (I). Specific and generic examples of such intermediates are given below. Further, such intermediates may include compounds according to formula (I), which may be used to produce another compound according to formula (I).

Throughout the following description of such processes it is to be understood that, where appropriate, suitable protecting groups will be attached to, and subsequently removed from, the various reactants and intermediates in a manner that will be readily understood by one skilled in the art of organic synthesis. Conventional procedures for using such protecting groups, as well as examples of suitable protecting groups, are well known within the art. Further such procedures and groups are described in the literature, such as in "Protective Groups in Organic Synthesis", 3rd ed., T. W. Green, P. G. M. Wuts, Wiley-Interscience, New York (1999).

It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis.

Examples of transformations are given below, and it is to be understood that the described transformations are not limited only to the generic groups or substituents for which the transformations are exemplified.

References and descriptions on other suitable transformations are for example given in "Comprehensive Organic Transformations—A Guide to Functional Group Preparations", 2nd ed., R. C. Larock, Wiley-VCH, New York (1999). References and descriptions of other suitable reactions are described in textbooks of organic chemistry well known to the one skilled in the art, such as "March's Advanced Organic Chemistry", 5th ed., M. B. Smith, J. March, John Wiley & Sons (2001) or, "Organic Synthesis", 2nd ed., M. B. Smith, McGraw-Hill, (2002).

Techniques for purification of intermediates and final products include for example, straight and reversed phase chromatography on column or rotating plate, size exclusion chromatography, re-crystallization, distillation and liquid-liquid or solid-liquid extraction, which will be readily understood by the one skilled in the art.

The terms "room temperature" and "ambient temperature" shall mean, unless otherwise specified, a temperature between 16 and 25° C. The term "reflux" shall mean, unless otherwise stated, in reference to an employed solvent using a temperature at or slightly above the boiling point of the named solvent. It is understood that microwaves can be used for the heating of reaction mixtures.

The terms "flash chromatography" or "flash column chromatography" shall mean preparative chromatography on silica using an organic solvent, or mixtures thereof, as mobile phase.

In the various schemes given below, generic groups, such as R-groups, have the same representation as given above herein, if not specifically defined.

It has been shown that the C-4 position (i.e. the position substituted with an methyl group) of the STAT3 inhibitory compound galiellalactone can be functionalized using selenium reagents starting from iso-galiellalactone but that this transformation results in inversion of the stereocenter (cf. PCT/EP2016/062437).

Interestingly, it was found that when iso-galiellalactone is sequentially treated with an aziridination reagent followed by a suitable base, a sulfonamide group is introduced into the C-4 position with retained relative stereochemistry of the methyl group:

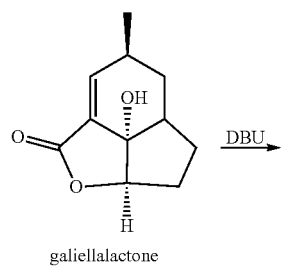

galiellalactone

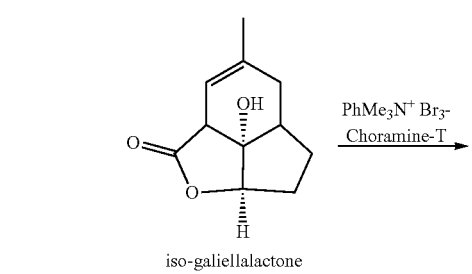

iso-galiellalactone

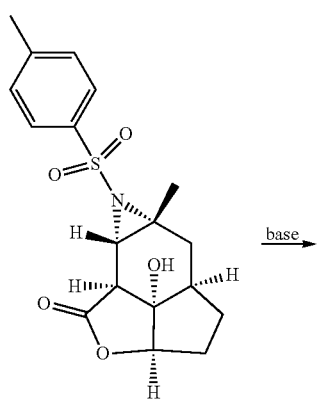

This is reaction enables the stereoselective addition of a sulfonamide group to the 4-position of galiellalactone, thus allowing the synthesis of novel galiellalactone based STAT3 inhibitors with improved properties.

Surprisingly when iso-galiellalactone is treated with $SeO_2$ under standard conditions for allylic oxidation (in dioxane or THF at ambient or elevated temperatures) the desired allylic alcohol or aldehyde were not obtained. However, heating a diluted solution of iso-galiellalactone in benzene (0.05 M or less) with $SeO_2$ produces the desired aldehyde.

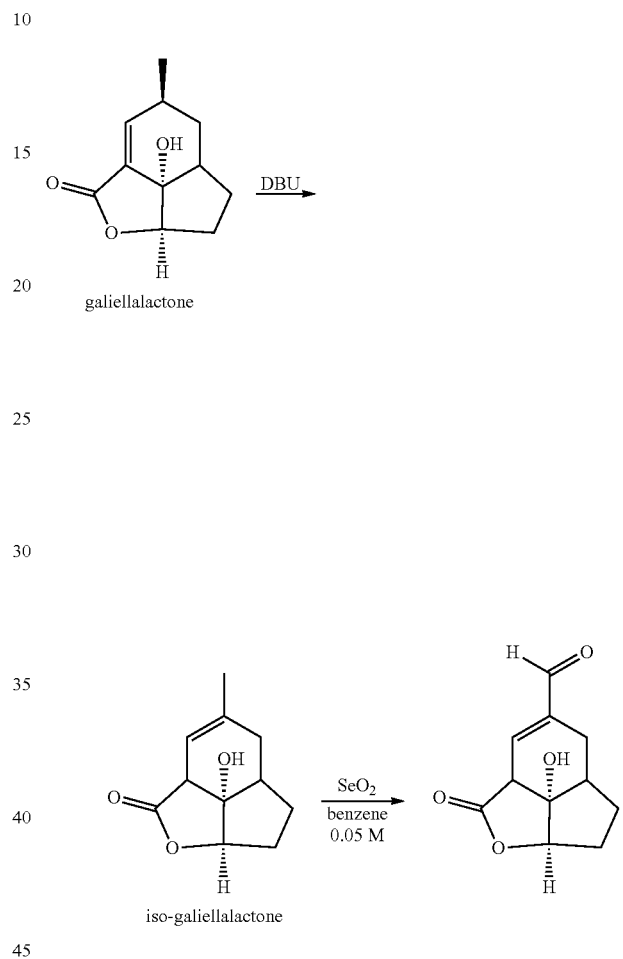

galiellalactone iso-galiellalactone

These reaction conditions can therefore be used to prepare oxidized intermediates that can further be derivatized to produce STAT3 inhibitors according to structure I.

Methods of Preparation of Final Compounds of Formula I by Aziridination of II Using N-Chloro-Sulfonamide Intermediates III Followed by Base Treatment (Scheme 1)

Scheme 1

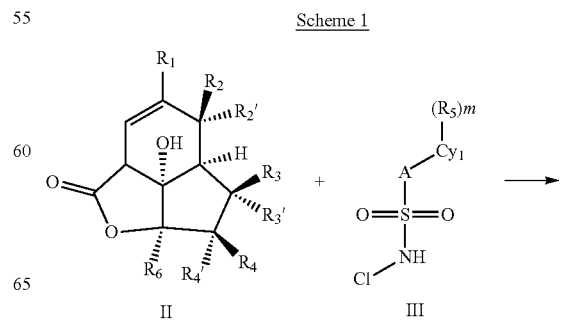

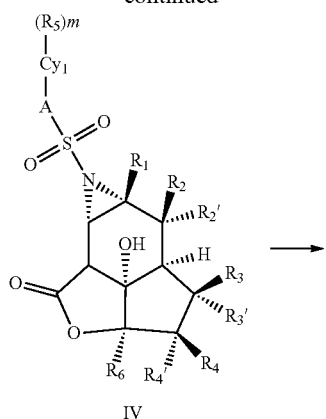

IV

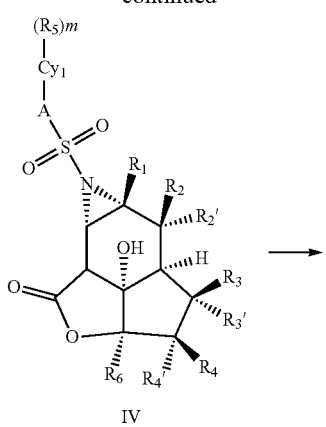

IV

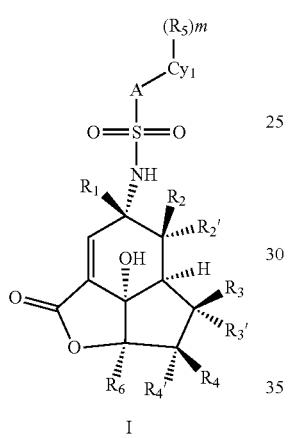

I

Formation of compounds of formula I, may be accomplished by aziridination of II using intermediate N-chloro sulfonamide III (as a salt or parent compound) in the presence of a suitable catalyst, e.g. 12 or $PhN^+Me_3Br_3^-$, under ambient conditions followed by treatment of the intermediate IV, which may or may not be isolated, with a suitable base to achieve a regioselective aziridine opening.

Methods of Preparation of Final Compounds of Formula I by Aziridination of II Using N-Iodo-Sulfonamide Intermediates V Followed by Base Treatment (Scheme 2)

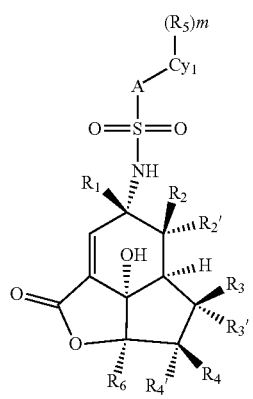

I

Formation of compounds of formula I, may be accomplished by aziridination of II using intermediate N-iodoaryl V in the presence of a suitable catalyst, e.g. $Cu(CF_3SO3)_2$, under suitable conditions followed by treatment with a suitable base to achieve a regioselective aziridine opening.

Methods of Preparation of Intermediates of Formula III (Scheme 3)

Scheme 2.

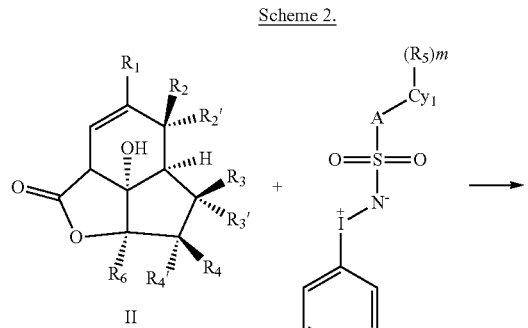

Scheme 3.

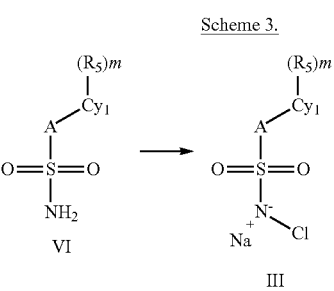

Intermediates of formula III may be prepared from VI by treatment with e.g. sodium hypochlorite or tertbutyl hypochlorite in the presence of sodium hydroxide and isolated as a sodium salt Methods of Preparation of Intermediates of Formula II
(Scheme 4)
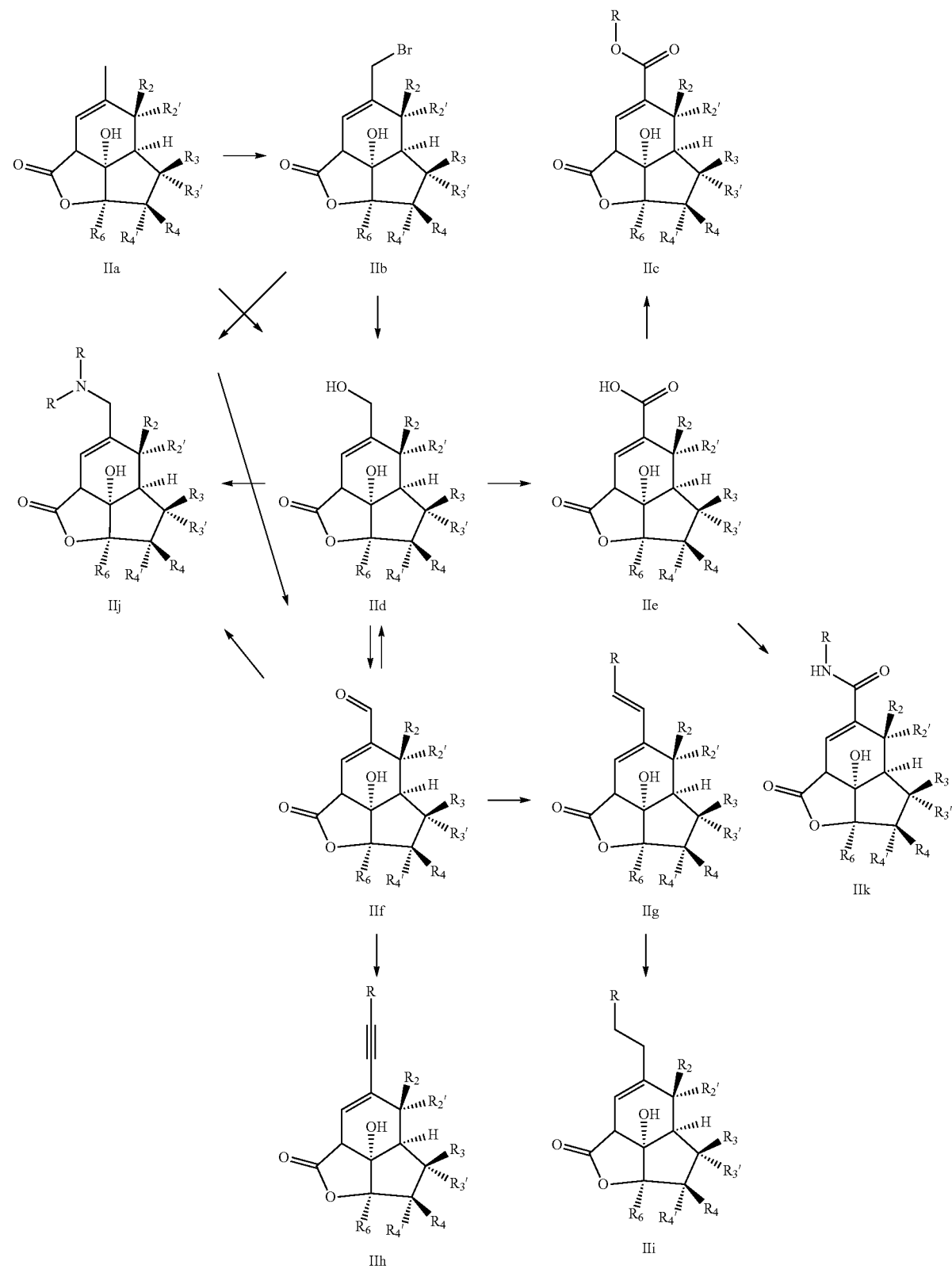

As schematically shown in Scheme 4, the methyl group in iso-galiellelactone, and derivatives thereof, may functionalized in various ways. As an example:

Intermediates IIb ($R_1$=—$CH_2Br$), IIf ($R_1$=—C(O)H) and IId ($R_1$=—$CH_2OH$) can be prepared by radical allylic bromination with NBS and allylic hydroxylation with $SeO_2$ respectively;

Alcohols IId can also be prepared through hydroxylation of IIb;

Alcohols IId can be oxidized to carboxylic acids IIe and aldehydes IIf with the use of appropriate oxidation reagents;

Esters IIc and amides IIk can be prepared from IIe through coupling thereto of alcohols and amines, respectively.

Alkenes IIg and alkynes IIH can be prepared from the aldehyde IIf.

Amines IIj can be prepared through nucleophilic substitution reactions starting from IIb and IId and an amine or through a reductive amination between aldehyde IIf and an amine.

Methods of Preparation of Intermediates of Formula II (Scheme 5)

Scheme 5

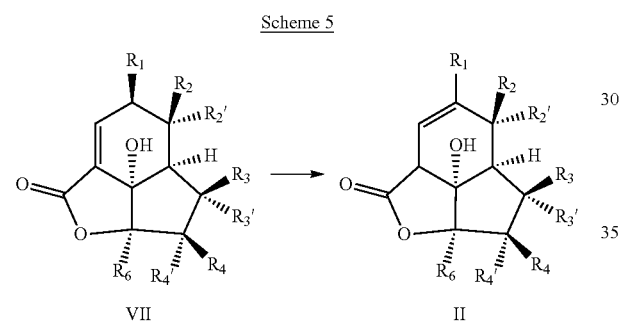

VII        II

Intermediates of formula II can be prepared by the isomerization of compounds of formula VII through the treatment with a suitable base, e.g. DBU. Compounds of formula VII can be prepared through synthetic methods described in Organic Letters 12, 22, 5100-3510 2010 and Journal of Antibiotics 55, 7, 663-665 2002.

Methods of Preparation of Final Compounds of Formula I by Sulfonamide Hydrolysis Followed by Sulfonylation (Scheme 6)

Scheme 6

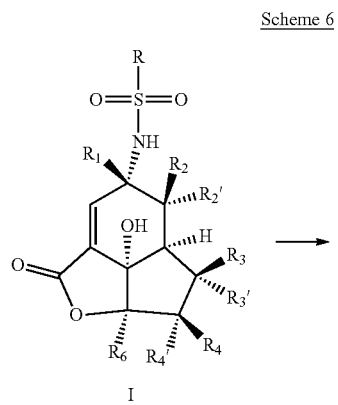

I

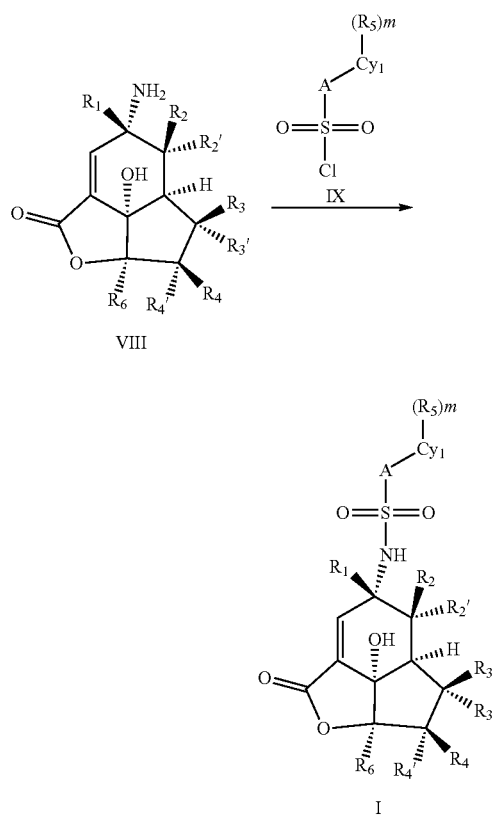

Intermediates of formula VIII can be prepared by sulfonamide hydrolysis or cleavage of compounds of formula I where R e.g. is tert-butyl, -4-methylphenyl, -4-nitrophenyl, -2,4-dinitrophenyl. When R is tert-butyl, triflic acid and anisole can be used. R is -4-methylphenyl, sodium/$NH_3$, HBr/HOAc or $SmI_2$ can be used. When R is -4-nitrophenyl or -2,4-dinitrophenyl thiophenol can be used. Final compounds of structure I can be prepared by sulfonylation of intermediate VIII using sulfonyl chlorides of structure IX.

Methods of Preparation of Final Compounds of Formula I by Lactone Hydrolysis Followed by a Sequential Oxidation/Grignard Addition Reaction (Scheme 7)

Scheme 7

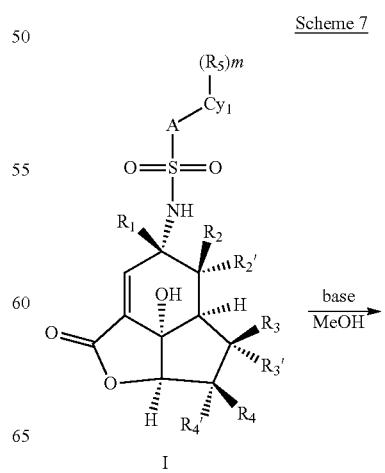

I

Methods of Preparation of Final Compounds of Formula I by a Reductive Amination Reaction (Scheme 8)

Scheme 8

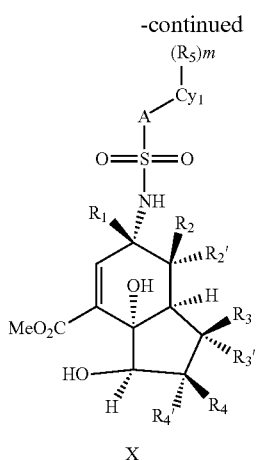

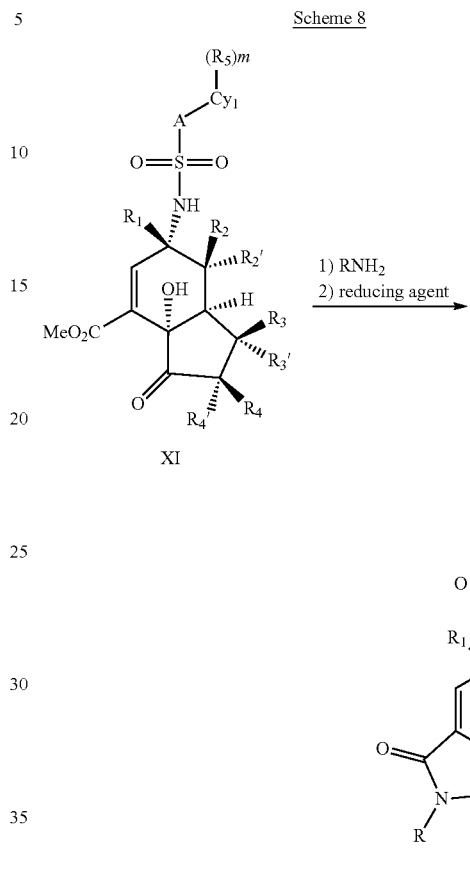

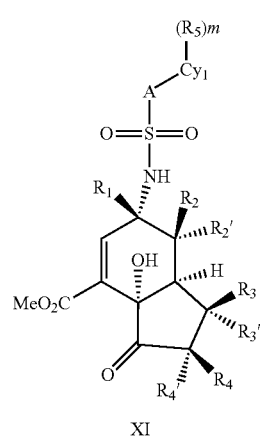

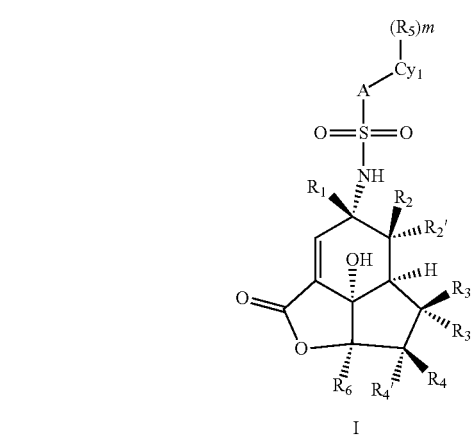

Intermediates of formula X can be prepared by lactone hydrolysis in methanol with a suitable base (e.g. trimethylamine). The following intermediate XI can be prepared by oxidation of the secondary hydroxyl group to a ketone. Swern oxidation conditions, TEMPO oxidation can be used. Final compounds of structure I can be prepared by addition of a suitable Grignard reagent where $R_6$ is C1-C5 alkyl and X is Cl, Br or I.

Final compounds of structure I can be prepared from intermediates of structure XI by reductive amination where a suitable amine (e.g. a benzylamine) is added sequentially or concomitantly with a reducing agent (e.g. $NaBH_4$, $NaCNBH_3$ or $NaBH(OAc)_3$) and with or without an agent that induces imine formation.

COMPOUND EXAMPLES

Abbreviations

AIBN Azobisisobutyronitrile
AZADO 2-Aza-adamantane-N-oxyl
DBU 1,8-Diazabicyclo[5.4.0]undec-7-ene
DMF N,N'-Dimethylformamide
DMP Dess-Martin periodinane
NBS N-bromo succinimide
THF Tetrahydrofurane
DMSO Dimethylsulfoxide
sat Saturated aqueous solution
Boc t-Butoxycarbonyl
TFA Trifluoroacetic acid
DMAP 4-Dimethylaminopyridine
h hour
r.t. room temperature
equiv equivalents
quant quantative
aq aqueous Ph phenyl
tol toluene
pyr pyridine General Material and Methods Preparative HPLC was performed on a Gilson system equipped with a UV detector using an XBridge Prep C-18 5 µm OBD, 19×50 mm column. Analytical HPLC-MS was performed using an Agilent 1100 series Liquid Chromatograph/Mass Selective Detector (MSD) (Single Quadropole) equipped with an electrospray interface and a UV diode array detector. Analyses were performed by two methods using either an ACE 3 C8 (3.0×50 mm) column with a gradient of acetonitrile in 0.1% aqueous TFA over 3 min and a flow of 1 mL/min, or an Xbridge C18 (3.0×50 mm) column with a gradient of acetonitrile in 10 mM ammonium bicarbonate over 3 min and a flow of 1 mL/min. $^1$H-NMR spectra were recorded on a Varian 400 MHz instrument at 25° C. The compounds have been named using the software MarvinSketch 14.11.24.0. In addition, the commercial names or trivial names were used for the commercial starting materials and reagents.

Preparation of Intermediates

Below follows non-limiting examples on the synthesis of intermediates useful for the preparation of compounds of formula I.

Intermediate 1

Sodium N-chloro-2-nitro-benzenesulfonamide

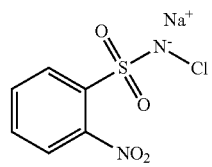 [SMILES: [Na+] ; O=[N+]([O-])c1ccccc1S(=O)(=O)[N-]Cl]

To a stirred solution of sodium hydroxide (98.9 mg, 2.47 mmol) in water (1.2 mL) was added 2-nitrobenzenesulfonamide (0.50 g, 2.47 mmol) at 0° C. To the reaction mixture was then added sodium hypochlorite (11-14%) (1.6 mL, 2.6 mmol) at 0° C. The reaction was then stirred at room temperature for 67 h. The precipitate was filtered off and washed with water and dried to give 360 mg (56%) of the product as a white solid. LCMS m/z 235 [M–H]$^-$-Na.

The intermediates 2-12 were prepared as described for sodium N-chloro-2-nitro-benzenesulfonamide (1). The reaction times were typically between 4-48 h and the reactions were followed by LCMS.

TABLE 1

| Intermediates 2 to 13 | | | | |
|---|---|---|---|---|
| Intermediate # | Structure | Name | LCMS (EST$^+$) m/z | Yield |
| 2 |  | Sodium N-chloro-4-methoxy-benzenesulfonamide | 220 [M – H]$^-$ – Na | 1.66 g (64%) |
| 3 |  | Sodium N-chloro-2-fluoro-benzenesulfonamide | 208 [M – H]$^-$ – Na | 360 mg (56%) |
| 4 |  | Sodium N-chloro-4-(trifluoromethyl)benzenesulfonamide | 258 [M – H]$^-$ – Na | 992 mg (53%) |
| 5 |  | Sodium N-chloro-benzenesulfonamide | 190 [M – H]$^-$ – Na | 510 mg (36%) |

TABLE 1-continued

Intermediates 2 to 13

| Intermediate # | Structure | Name | LCMS (ESI+) m/z | Yield |
|---|---|---|---|---|
| 6 | 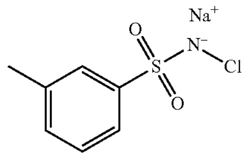 | Sodium N-chloro-3-methyl-benzenesulfonamide | 204 [M − H]− − Na | 447 mg (21%) |
| 7 | 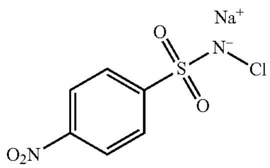 [SMILES: [Na+] ; O=[N+]([O-])c1ccc(S(=O)(=O)[N-]Cl)cc1] | Sodium N-chloro-4-nitro-benzenesulfonamide | 235 [M − H]− − Na | 821 mg (64%) |
| 8 | 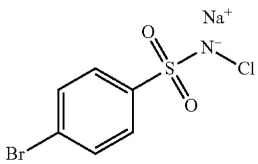 [SMILES: [Na+] ; O=S(=O)([N-]Cl)c1ccc(Br)cc1] | Sodium N-chloro-5-methyl-pyridine-2-sulfonamide | 268, 270 [M − H]− − Na | 824 mg (63%) |
| 9 | 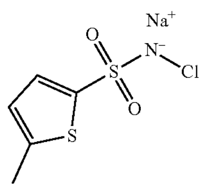 | Sodium N-chloro-5-methyl-thiophene-2-sulfonamide | 229 [M + H]+ | 93 mg (34%) |
| 10 | 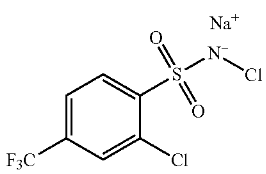 [SMILES: [Na+] ; O=S(=O)([N-]Cl)c1ccc(C(F)(F)F)cc1Cl] | Sodium N,2-dichloro-4-(trifluoromethyl)benzenesulfonamide | 292 [M − H]− − Na | 93 mg (42%) |
| 11 | 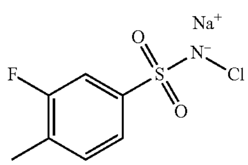 | Sodium N-chloro-3-fluoro-4-methyl-benzenesulfonamide | 222 [M − H]− − Na | 88 mg (63%) |
| 12 | 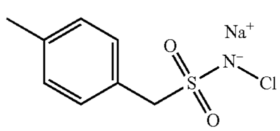 | Sodium N-chloro-1-(p-tolyl)methanesulfonamide | 218 [M − H]− − Na | 98 mg (37%) |
| 13 | 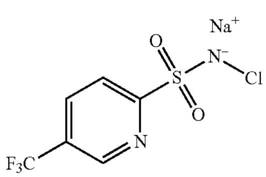 [SMILES: [Na+] ; O=S(=O)([N-]Cl)c1ccc(C(F)(F)F)cn1] | Sodium N-chloro-5-(trifluoromethyl)pyridine-2-sulfonamide | 259 [M + H]+ − Na | |

Method B

Intermediate 14 tert-Butyl hypochlorite

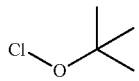

The reaction and workup were performed in the dark behind a blast shield since the product is heat and light sensitive. To a vigorously stirred solution of NaOCl (1.39 mL, 2.70 mmol) (11-14%) at 0° C. was added a mixture of 2-methylpropan-2-ol (7) (254 uL, 2.70 mmol) and acetic acid (164 uL, 2.83 mmol) in one portion. The reaction was vigorously stirred at 0° C. for 15 min. The reaction was poured into a separating funnel. The organic phase (product) was separated and washed successively with 10% aqueous potassium carbonate and dried over calcium chloride to give about 190 μL of the product as a yellow liquid. Used in the next step without further purification.

Intermediate 15

Sodium N-chloro-5-methyl-pyridine-2-sulfonamide

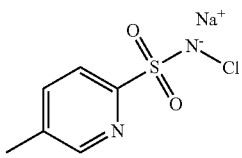

To a mixture of 5-methylpyridine-2-sulfonamide (109 mg, 0.63 mmol) in 1 M aqueous NaOH (0.63 mL, 0.63 mmol) was added tert-butyl hypochlorite (86 uL, 0.76 mmol) and the reaction stirred at room temperature for 1.5 h in the dark. The reaction was evaporated and the desired product washed with diethyl ether and dried under reduced pressure to yield the crude product. Used in the next step without further purification. It was assumed that the reaction gave quantitative yield. LCMS m/z 207 $[M+H]^+$-Na.

The intermediates 16-18 were prepared as described for sodium N-chloro-5-methyl-pyridine-2-sulfonamide (15). The reaction times were typically between 1-5 h and the reactions were followed by LCMS.

TABLE 2

| | Intermediates 16 to 18 | | |
|---|---|---|---|
| Intermediate # | Structure | Name | MS (ESI$^+$) m/z |
| 16 | | Sodium N-chloro-4-cyano-benzenesulfonamide | 215 $[M - H]^-$ - Na |
| 17 | | Sodium N-chloropropane-2-sulfonamide | 156 $[M - H]^-$ - Na |
| 18 | | Sodium N-chloro-6-methyl-pyridine-3-sulfonamide | 207 $[M + H]^+$ - Na |

Intermediate 19

Sodium N-chloro-4-(4,5-dihydrooxazol-2-yl)benzenesulfonamide

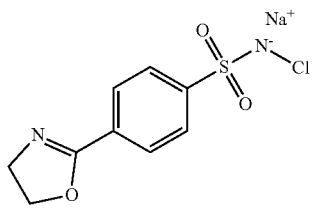

a) 4-(4,5-Dihydrooxazol-2-yl)benzenesulfonamide

Literature reference: *J. Org. Chem.* 2014, 79, 8668-8677.

To a solution of methanol (2 mL) were added 2-aminoethanol (0.83 mL, 13.7 mmol) and potassium carbonate (379 mg, 2.74 mmol) and the solution stirred for 30 min. 4-Cyanobenzenesulfonamide (0.50 g, 2.74 mmol) was added and the reaction stirred at 80° C. for 24 h. The methanol was removed in vacuo and 2 M $NH_4Cl$ (aq.) was added and the precipitate was filtered off, washed with water and diethyl ether and dried to give 556 mg (90%) of the crude product. LCMS (ESI$^+$) m/z 225 [M−H]$^-$.

b) Sodium N-chloro-4-(4,5-dihydrooxazol-2-yl)benzenesulfonamide

Prepared according to sodium N-chloro-2-nitro-benzenesulfonamide. Starting from 4-(4,5-dihydrooxazol-2-yl)benzenesulfonamide (154 mg, 0.68 mmol) gave 90 mg (47%) of the title compound. LCMS (ESI$^+$) m/z 261 [M+H]$^+$-Na.

Preparation of Final Compounds

Example 1

N-[(4R,7R,9R,11S)-11-Hydroxy-9-methyl-2-oxo-3-oxatricyclo[5.3.1.0$^{4,11}$]undec-1(10)-en-9-yl]-4-methylbenzene-1-sulfonamide

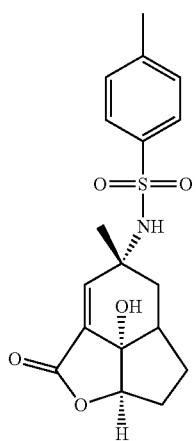

a) (1R,4R,8R,10S,12S)-12-Hydroxy-10-methyl-9-[(4-sulfonamide)sulfonyl]-5-oxa-9-azatetracyclo[5.4.1.04,12.0$^{8,10}$]dodecan-6-one Literature reference: *Org. Biomol. Chem.* 2008, 6, 4299-4314.

Under nitrogen iso-galiellalactone ((4R,7R,11S)-11-hydroxy-9-methyl-3-oxatricyclo[5.3.1.0$^{4,11}$]undec-9-en-2-one) (414 mg, 2.13 mmol, 1 equiv.) and Chloramine-T (660 mg, 2.35 mmol) were suspended in acetonitrile (5 mL). Then trimethylphenylammonium tribromide (80 mg, 0.21 mmol) was added under stirring and the reaction was stirred at room temperature overnight. The reaction mixture was concentrated and the crude was used as such in the next step.

b) N-[(4R,7R,9S,11S)-11-Hydroxy-9-methyl-2-oxo-3-oxatricyclo[5.3.1.0$^{4,11}$]undec-1(10)-en-9-yl]-4-methylbenzene-1-sulfonamide Under nitrogen to the concentrated reaction mixture of (1R,4R,8R,10S,12S)-12-Hydroxy-10-methyl-9-[(4-sulfonamide)sulfonyl]-5-oxa-9-azatetracyclo[5.4.1.04,12.0$^{8,10}$]dodecan-6-one (774 mg, 2.13 mmol) was added THF (5 mL) and 1,8-Diazabicyclo[5.4.0]undec-7-ene (DBU) (0.32 mL, 2.13 mmol). The reaction mixture was stirred at rt for 12 h. Dichloromethane was added to the reaction mixture. The organic phase was then washed with 1 M aqueous HCl, dried over magnesium sulfate, filtered and concentrated. The crude product was purified by silica gel flash chromatography (eluent: EtOAc:Heptrane 2:1) Fractions containing product were collected and concentrated. However, no fractions were entirely pure but contained a by-product ([M+H]$^+$=535, [M−H]$^-$=533). The concentrated fractions were dissolved in acetonitrile and purified by preparatory HPLC (eluent: Acetonitrile 5% to 35%/TFA (aq (0.1%)). The fractions were collected quickly and concentrated under vacuum at room temperature. Dichloromethane was added and the water phase was extracted 2 times with $CH_2Cl_2$. The organic phase was dried with $MgSO_4$, filtered and concentrated to give 200 mg (26% yield, 99% purity) of the product. $^1$H NMR (400 MHz, CDCl$_3$): δ=1.28 (s, 1H), 1.34 (s, 3H), 1.69 (m, 2H), 1.81 (m, 1H), 2.06 (m, 1H), 2.25 (m, 2H), 2.42 (s, 3H), 2.50 (m, 1H), 2.75 (dd, J=15.44 Hz, J=6.18 Hz, 1H), 3.83 (dd, J=8.17 Hz, J=2.30 Hz, 1H), 5.16 (, 1H, NH). 6.33 (s, 1H), 7.30 (d, J=8.29 Hz, 2H), 7.67 (d, J=8.29 Hz, 2H). LCMS (ESI$^+$) m/z 362 [M−H]$^-$.

Below follow non-limiting examples on the synthesis of final compounds of formula I.

General Methods

General Method A

In Scheme 7 below, the general procedure for the synthesis of 4-N galiellalactone sulfonamides used to provide examples 2-20 is provided.

Scheme 7

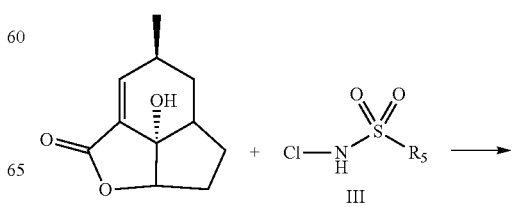

-continued

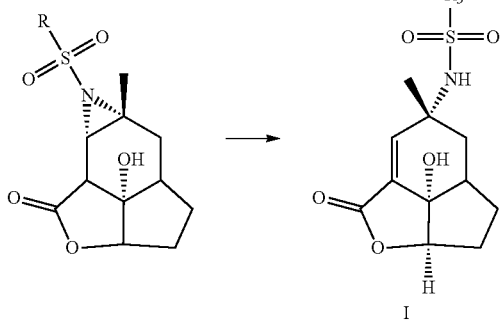

The examples 2-20 were prepared as described for N-[(4R,7R,9R,11S)-11-hydroxy-9-methyl-2-oxo-3-oxatricyclo[5.3.1.0^{4,11}]undec-1(10)-en-9-yl]-4-methylbenzene-1-sulfonamide (example 1). Typically, the products were purified by preparative HPLC.

Iso-galiellalactone (1.0 eq.) and the corresponding N-chloro sulfonamide (1.1 eq.) were suspended in acetonitrile. Then trimethylphenylammonium tribromide (0.1 eq.) was added under stirring and the reaction was stirred at room temperature overnight. The reaction mixture was concentrated and the crude was used as such in the next step.

The concentrated crude reaction product from the previous step was dissolved in THF under a nitrogen atmosphere and 1,8-diazabicyclo[5.4.0]undec-7-ene (DBU) (1.0 eq.) was added. The reaction mixture was stirred at rt for 12 h. Dichloromethane was added to the reaction mixture. The organic phase was then washed with 1 M aqueous HCl, dried over magnesium sulfate, filtered and concentrated. The crude product was purified by silica gel flash chromatography (eluent: EtOAc:Heptrane 2:1) or purified by preparatory HPLC (eluent: Acetonitrile 5% to 35%/TFA (aq (0.1%))

(yield and analytical data given for each compound).

TABLE 4

Examples 2 to 20

| Example | Structure | Name | Yield | MS (ESI+) m/z | NMR |
|---|---|---|---|---|---|
| 2 | 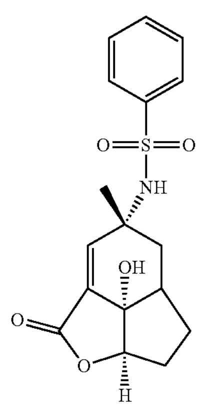 | N-[(4R,7R,9R,11S)-11-Hydroxy-9-methyl-2-oxo-3-oxatricyclo[5.3.1.0^{4,11}]undec-1(10)-en-9-yl]benzenesulfonamide | 30 mg (56%) | 348 [M − H]− | $^1$H NMR (400 MHz, CDCl$_3$): δ = 7.82 (m, 2H), 7.62 (m, 1H), 7.53 (m, 2H), 6.33 (s, 1H), 4.85 (dd, J = 8.2 Hz, J = 2.2 Hz, 1H), 2.77 (dd, J = 14.9 Hz, J = 6.3 Hz, 1H), 2.52 (m, 1H), 2.08 (m, 1H), 1.83 (m, 1H), 1.71 (m, 2H), 1.37 (s, 3H), 1.35-1.24 (m, 1H). |
| 3 | 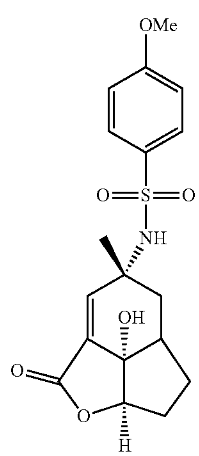 | N-[(4R,7R,9R,11S)-11-Hydroxy-9-methyl-2-oxo-3-oxatricyclo[5.3.1.0^{4,11}]undec-1(10)-en-9-yl]-4-methoxybenzene-1-sulfonamide | 7.0 mg (11%) | 378 [M − H]− | $^1$H NMR (400 MHz, CDCl$_3$): δ = 7.73 (d, J = 9.0 Hz, 2H), 6.98 (d, J = 9.0 Hz, 2H), 6.30 (s, 1H), 4.86 (dd, J = 8.0 Hz, J = 2.1 Hz, 1H), 2.78 (dd, J = 14.9 Hz, J = 6.4 Hz, 1H), 2.51 (m, 1H), 2.08 (m, 1H), 1.82 (m, 1H), 1.74-1.68 (m, 2H), 1.35 (s, 3H), 1.34-1.27 (m, 1H). |

TABLE 4-continued

Examples 2 to 20

| Example | Structure | Name | Yield | MS (ESI+) m/z | NMR |
|---|---|---|---|---|---|
| 4 | 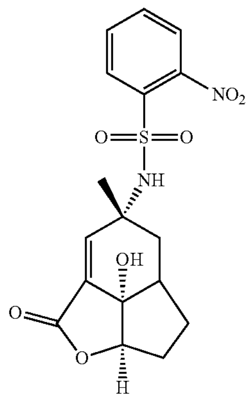 | N-[(4R,7R,9R,11S)-11-Hydroxy-9-methyl-2-oxo-3-oxatricyclo[5.3.1.0$^{4,11}$]undec-1(10)-en-9-yl]-2-nitrobenzene-1-sulfonamide | 7 mg (28%) | 393 [M − H]$^-$ | $^1$H NMR (400 MHz, CDCl$_3$): δ = 8.00 (m, 1H), 7.81 (m, 1H), 7.72 (m, 2H), 6.53 (s, 1H), 4.78 (m, 1H), 2.78-2.64 (m, 1H), 2.49 (m, 1H), 2.06 (m, 1H), 1.82 (m, 1H), 1.66 (m, 2H), 1.43 (s, 3H), 1.34 (m, 1H). |
| 5 | 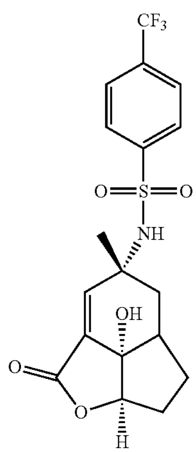 | N-[(4R,7R,9R,11S)-11-Hydroxy-9-methyl-2-oxo-3-oxatricyclo[5.3.1.0$^{4,11}$]undec-1(10)-en-9-yl]-4-(trifluoromethyl)benzene-1-sulfonamide | 6 mg (56%) | 416 [M − H]$^-$ | $^1$H NMR (400 MHz, CDCl$_3$): δ = 7.96 (d, J = 8.2 Hz, 2H), 7.80 (d, J = 8.2 Hz, 2H), 6.47 (s, 1H), 5.51 (bs, 1H), 4.88 (dd, J = 8.1 Hz, J = 2.2 Hz, 1H), 2.74 (dd, J = 15.0 Hz, J = 6.4 Hz, 1H), 2.55 (m, 1H), 2.10 (m, 1H), 1.86 (m, 1H), 1.78-1.65 (m, 2H), 1.39 (s, 3H), 1.29 (m, 1H). |
| 6 | 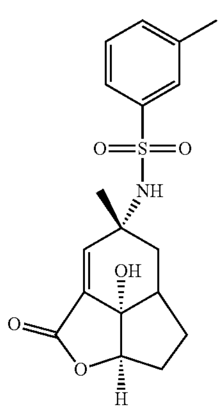 | N-[(4R,7R,9R,11S)-11-Hydroxy-9-methyl-2-oxo-3-oxatricyclo[5.3.1.0$^{4,11}$]undec-1(10)-en-9-yl]-3-methylbenzene-1-sulfonamide | 2 mg (40%) | 362 [M − H]$^-$ | $^1$H NMR (400 MHz, CDCl$_3$): δ = 7.61 (m, 2H), 7.41 (m, 2H), 6.31 (s, 1H), 5.18 (bs, 1H), 4.86 (dd, J = 8.1 Hz, J = 2.2 Hz, 1H), 2.78 (dd, J = 15.0 Hz, J = 6.2 Hz, 1H), 2.52 (m, 1H), 2.44 (s, 3H), 2.08 (m, 1H), 1.82 (m, 1H), 1.72 (m, 2H), 1.37 (s, 3H), 1.30 (m, 1H). |

TABLE 4-continued

Examples 2 to 20

| Example | Structure | Name | Yield | MS (ESI+) m/z | NMR |
|---|---|---|---|---|---|
| 7 | 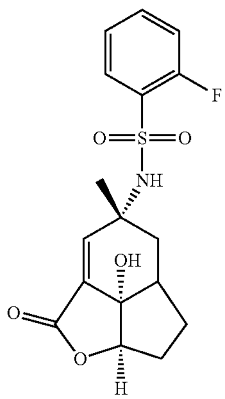 | 2-Fluoro-N-[(4R,7R,9R,11S)-11-hydroxy-9-methyl-2-oxo-3-oxatricyclo[5.3.1.0$^{4,11}$]undec-1(10)-en-9-yl]benzene-1-sulfonamide | 30 mg (53%) | 366 [M − H]$^-$ | $^1$H NMR (400 MHz, CDCl$_3$): δ = 7.74 (m, 1H), 7.64 (m, 1H), 7.31 (m, 1H), 7.27-7.20 (m, 1H), 6.11 (s, 1H), 5.40 (bs, 1H), 4.85 (dd, J = 8.3 Hz, J = 1.7 Hz, 1H), 2.81 (dd, J = 15.1 Hz, J = 6.2 Hz, 1H), 2.51 (m, 1H), 2.07 (m, 1H), 1.83-1.76 (m, 2H), 1.75-1.68 (m, 1H), 1.39 (s, 3H), 1.36-1.22 (m, 1H). |
| 8 | 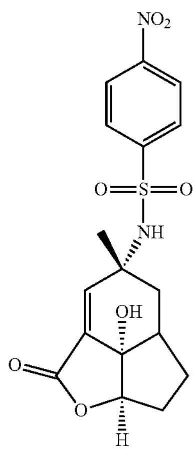 | N-[(4R,7R,9R,11S)-11-Hydroxy-9-methyl-2-oxo-3-oxatricyclo[5.3.1.0$^{4,11}$]undec-1(10)-en-9-yl]-4-nitrobenzene-1-sulfonamide | 4 mg (39%) | 393 [M − H]$^-$ | $^1$H NMR (400 MHz, CDCl$_3$): δ = 8.37 (d, J = 9.0 Hz, 2H), 8.01 (d, J = 9.0 Hz, 2H), 6.47 (s, 1H), 5.60 (bs, 1H), 4.88 (dd, J = 7.9 Hz J = 2.0 Hz 1H), 2.73 (dd, J = 15.0 Hz, J = 6.6 Hz, 1H), 2.56 (m, 1H), 2.17-2.04 (m, 1H), 1.87 (m, 1H), 1.79-1.66 (m, 2H), 1.41 (s, 3H), 1.36-1.26 (m, 1H). |
| 9 | 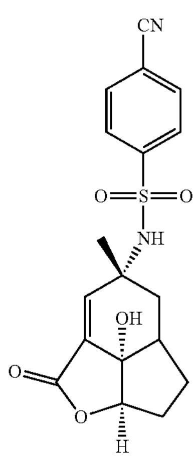 | 4-Cyano-N-[(4R,7R,9R,11S)-11-hydroxy-9-methyl-2-oxo-3-oxatricyclo[5.3.1.0$^{4,11}$]undec-1(10)-en-9-yl]benzene-1-sulfonamide | 5 mg (25%) | 373 [M − H]$^-$ | $^1$H NMR (400 MHz, CDCl$_3$): δ = 7.95 (d, J = 8.7 Hz, 2H), 7.83 (d, J = 8.7 Hz, 2H), 6.47 (s, 1H), 5.68 (bs, 1H), 4.88 (dd, J = 8.1 Hz, J = 1.9 Hz, 1H), 2.71 (dd, J = 15.3 Hz, J = 6.6 Hz, 1H), 2.55 (m, 1H), 2.18-2.04 (m, 1H), 1.87 (m, 1H), 1.76 (m, 1H), 1.66 (m, 1H), 1.40 (s, 3H), 1.30 (m, 1H). |

TABLE 4-continued

| | | | | MS (ESI+) | |
|---|---|---|---|---|---|
| Example | Structure | Name | Yield | m/z | NMR |

Examples 2 to 20

| 10 | | 4-Bromo-N-[(4R,7R,9R,11S)-11-hydroxy-9-methyl-2-oxo-3-oxatricyclo[5.3.1.0⁴,¹¹]undec-1(10)-en-9-yl]benzene-1-sulfonamide | 9 mg (51%) | 426, 428 [M − H]⁻ | $^1$H NMR (400 MHz, CDCl$_3$): δ = 7.67 (s, 4H), 6.41 (s, 1H), 5.23 (bs, 1H), 4.87 (dd, J = 8.1 Hz, J = 2.1 Hz, 1H), 2.75 (dd, J = 15.5 Hz, J = 6.2 Hz, 1H), 2.53 (m, 1H), 2.09 (m, 1H), 1.84 (m, 1H), 1.72 (m, 2H), 1.38 (s, 3H), 1.30 (m, 1H). |
| 11 | | 4-(4,5-Dihydro-1,3-oxazol-2-yl)-N-[(4R,7R,9R,11S)-11-hydroxy-9-methyl-2-oxo-3-oxatricyclo[5.3.1.0⁴,¹¹]undec-1(10)-en-9-yl]benzene-1-sulfonamide | 2.6 mg (5%) | 417 [M − H]⁻ | |
| 12 | | N-[(4R,7R,9R,11S)-11-Hydroxy-9-methyl-2-oxo-3-oxatricyclo[5.3.1.0⁴,¹¹]undec-1(10)-en-9-yl]-5-methylpyridine-2-sulfonamide | 25 mg (45%) | 363 [M − H]⁻ | $^1$H NMR (400 MHz, CDCl$_3$): δ = 8.47 (m, 1H), 7.83 (d, J = 7.8 Hz, 1H), 7.74 (m, 1H), 6.18 (s, 1H), 5.72 (bs, 1H), 4.82 (dd, J = 8.0 Hz, J = 2.9 Hz, 1H), 2.71 (dd, J = 15.0 Hz, J = 6.7 Hz, 1H), 2.52 (m, 1H), 2.45 (s, 3H), 2.07 (m, 1H), 1.85 (m, 1H), 1.64 (m, 2H), 1.51 (s, 3H), 1.24 (m, 1H). |

TABLE 4-continued

Examples 2 to 20

| Example | Structure | Name | Yield | MS (ESI+) m/z | NMR |
|---|---|---|---|---|---|
| 13 | 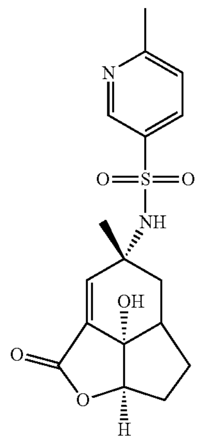 | N-[(4R,7R,9R,11S)-11-Hydroxy-9-methyl-2-oxo-3-oxatricyclo[5.3.1.0⁴,¹¹]undec-1(10)-en-9-yl]-6-methylpyridine-3-sulfonamide | 30 mg (55%) | 363 [M − H]⁻ | ¹H NMR (400 MHz, CDCl₃): δ: MR (400 MHz, CDCl3 (d, J = 7.8 Hz, 1H), 7.74 (m, 1H), 6.18 (s, 1H), 5.72 (bs, 1H), 4.8 1.85 (m, 1H), 1.64 (m, 2H), 1.56 (dd, J = 8.0 Hz, J = 2.0 Hz, 1H), 2.72 (dd, J = 14.8 Hz, J = 6.7 Hz, 1H), 2.68 |
| 14 | 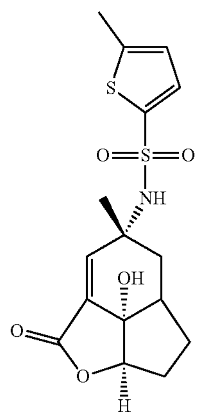 | N-[(4R,7R,9R,11S)-11-Hydroxy-9-methyl-2-oxo-3-oxatricyclo[5.3.1.0⁴,¹¹]undec-1(10)-en-9-yl]-5-methylthiophene-2-sulfonamide | 5.3 mg (8%) | 368 [M − H]⁻ | |
| 15 | 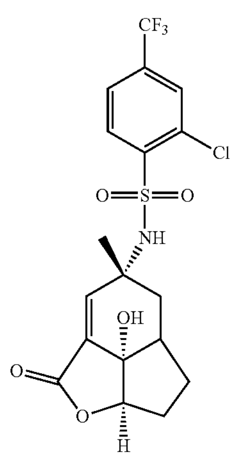 | 2-Chloro-N-[(4R,7R,9R,11S)-11-hydroxy-9-methyl-2-oxo-3-oxatricyclo[5.3.1.0⁴,¹¹]undec-1(10)-en-9-yl]-4-(trifluoromethyl)benzene-1-sulfonamide | 2.7 mg (5.8%) | 450 [M − H]⁻ | ¹H NMR (400 MHz, CDCl₃): δ = 8.05 (d, J = 8.4 Hz, 1H), 7.82 (d, J = 1.4 Hz, 1H), 7.02 (d, J = 8.4 Hz, 1H), 6.11 (s, 1H), 5.63 (brs, 1H), 4.87 (dd, J = 8.3 Hz, J = 1.7 Hz, 1H), 2.79 (dd, J = 15.1 Hz, J = 6.1 Hz, 1H), 2.52 (m, 1H), 2.08 (m, 1H), 1.86-1.77 (m, 2H), 1.76-1.69 (m, 1H), 1.40 (s, 3H), 1.32 (m, 1H) |

TABLE 4-continued

Examples 2 to 20

| Example | Structure | Name | Yield | MS (ESI+) m/z | NMR |
|---|---|---|---|---|---|
| 16 | 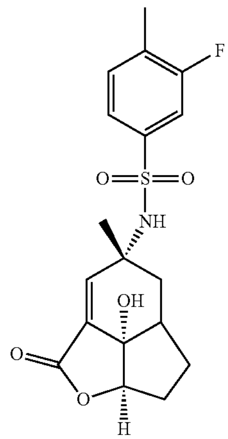 | 3-Fluoro-N-[(4R,7R,9R,11S)-11-hydroxy-9-methyl-2-oxo-3-oxatricyclo[5.3.1.0$^{4,11}$]undec-1(10)-en-9-yl]-4-methylbenzene-1-sulfonamide | 13.9 mg (29%) | 380 [M − H]$^-$ | $^1$H NMR (400 MHz, CDCl$_3$): δ = 7.48 (td, 2H), 7.34 (t, 1H), 6.40 (s, 1H), 5.30 (brs, 1H), 4.86 (dd, J = 8.1 Hz, J = 1.9 Hz, 1H), 2.75 (dd, J = 15.4 Hz, J = 6.5 Hz, 1H), 2.53 (m, 1H), 2.36 (s, 3H), 2.09 (m, 1H), 1.84 (m, 1H), 1.76-1.66 (m, 2H), 1.38 (s, 3H), 1.29 (m, 1H). |
| 17 | 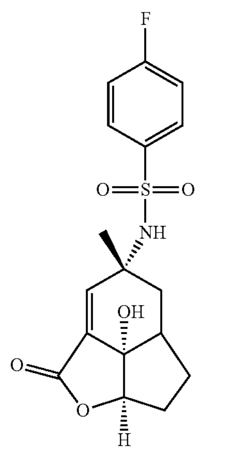 | 4-Fluoro-N-[(4R,7R,9R,11S)-11-hydroxy-9-methyl-2-oxo-3-oxatricyclo[5.3.1.0$^{4,11}$]undec-1(10)-en-9-yl]benzene-1-sulfonamide | | | $^1$H NMR (500 MHz, CDCl$_3$): δ = 7.86 (dd, J = 5.0 Hz, J = 9.0 Hz, 2H), 7.21 (dd, J = 8.2 Hz, J = 9.0 Hz, 2H), 6.50 (s, 1H), 5.81 (brs, 1H), 4.87 (dd, J = 2.3 Hz, J = 7.8 Hz, 1H), 2.70 (dd, J = 6.9 Hz, J = 14.9 Hz, 1H), 2.55 (m, 1H), 2.10 (m, 1H), 1.87 (m, 1H), 1.73 (m, 1H), 1.61 (dd, J = 3.7 Hz, J = 14.9 Hz, 1H), 1.39 (s, 3H), 1.28 (m, 1H) |
| 18 | 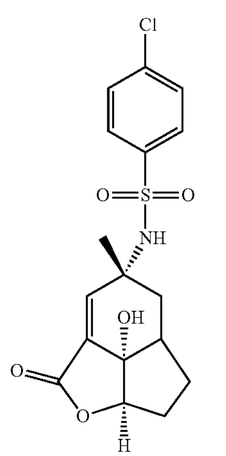 | 4-Chloro-N-[(4R,7R,9R,11S)-11-hydroxy-9-methyl-2-oxo-3-oxatricyclo[5.3.1.0$^{4,11}$]undec-1(10)-en-9-yl]benzene-1-sulfonamide | | | $^1$H NMR (500 MHz, CDCl$_3$): δ = 7.88 (d, J = 8.9 Hz, 2H), 7.21 (d, J = 8.9 Hz, 2H), 6.54 (s, 1H), 5.83 (brs, 1H), 4.87 (dd, J = 2.3 Hz, J = 7.9 Hz, 1H), 2.69 (dd, J = 6.7 Hz, J = 14.9 Hz, 1H), 2.55 (m, 1H), 2.10 (m, 1H), 1.87 (m, 1H), 1.74 (m, 1H), 1.61 (dd, J = 3.7 Hz, J = 14.9 Hz, 1H), 1.39 (s, 3H), 1.28 (m, 1H) |

TABLE 4-continued

Examples 2 to 20

| Example | Structure | Name | Yield | MS (ESI+) m/z | NMR |
|---|---|---|---|---|---|
| 19 | 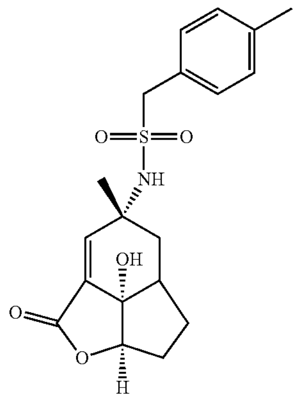 | N-[(4R,7R,9R,11S)-11-Hydroxy-9-methyl-2-oxo-3-oxatricyclo[5.3.1.0$^{4,11}$]undec-1(10)-en-9-yl]-1-(4-methylphenyl)methanesulfonamide | 22 mg (31%) | 376 [M − H]$^-$ | $^1$H NMR (400 MHz, CDCl$_3$): δ = 7.26 (d, J = 8.0 Hz, 2H), 7.21 (d, J = 8.0 Hz, 2H), 6.48 (s, 1H), 4.86 (d, J = 8.0 Hz, 1H), 4.57 (bs, 1H), 4.24 (d, J = 14.0 Hz, 1H), 4.21 (d, J = 14.0 Hz, 1H), 2.72 (dd, J = 15.3 Hz, J = 6.2 Hz, 1H), 2.46 (m, 1H), 2.38 (s, 3H), 2.06 (m, 1H), 1.80-1.72 (m, 3H), 1.34 (s, 3H), 1.28 (m, 1H) |
| 20 | 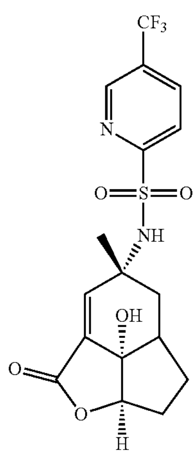 | N-[(4R,7R,9R,11S)-11-hydroxy-9-methyl-2-oxo-3-oxatricyclo[5.3.1.0$^{4,11}$]undec-1(10)-en-9-yl]-5-(trifluoromethyl)pyridine-2-sulfonamide | 13.8 mg (26%) | 417 [M − H]$^-$ | $^1$H NMR (400 MHz, CDCl$_3$): δ = 8.96 (m, 1H), 8.21 (ddd, J = 8.2 Hz, J = 2.2 Hz, J = 0.6 Hz, 1H), 8.05 (d, J = 8.1 Hz, 1H), 6.19 (s, 1H), 5.61 (brs, 1H), 4.85 (dd, J = 8.0 Hz, J = 2.4 Hz, 1H), 2.77 (dd, J = 15.3 Hz, J = 6.3 Hz, 1H), 2.53 (m, 1H), 2.09 (m, 1H), 1.85 (m, 1H), 1.76 (dd, J = 15.3 Hz, J = 3.7 Hz, 1H), 1.69 (m, 1H), 1.50 (s, 3H), 1.28 (m, 1H) |

Example 21

4-Amino-N-[(4R,7R,9R,11S)-11-hydroxy-9-methyl-2-oxo-3-oxatricyclo[5.3.1.0⁴,¹¹]undec-1(10)-en-9-yl]benzene-1-sulfonamide

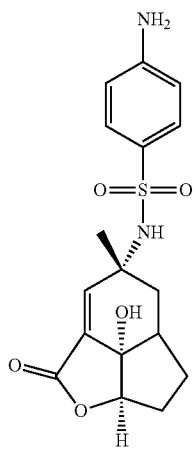

N-[(4R,7R,9R,11S)-11-Hydroxy-9-methyl-2-oxo-3-oxatricyclo[5.3.1.0⁴,¹¹]undec-1(10)-en-9-yl]-4-nitrobenzene-1-sulfonamide (16.4 mg, 0.042 mmol) was mixed in dry DMF (0.04 mL) and tin(II) chloride dihydrate (187.7 mg, 0.832 mmol) was added. The reaction mixture was stirred overnight at room temperature. Acetonitrile was added to the reaction mixture and the crude product was purified by preparatory HPLC with acetonitrile (gradient from 5 to 35% in 12 min): TFA (aq 0.1%). The product was collected and extracted with CH$_2$Cl$_2$ (3×). The organic phase was dried (MgSO$_4$), filtered and concentrated under vacuum to give 15 mg (98%) of the title compound. LCMS (ESI$^+$) m/z 363 [M−H]$^-$.

Example 22

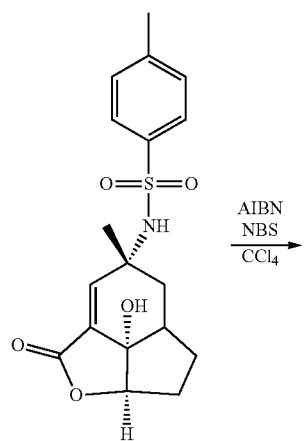

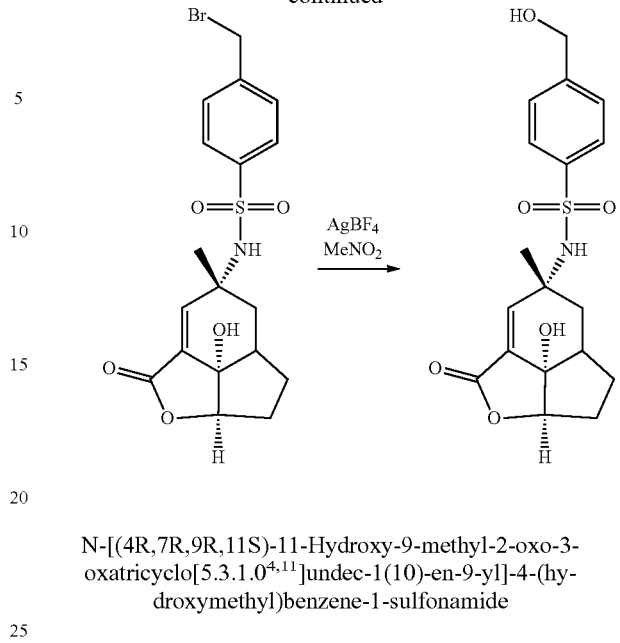

N-[(4R,7R,9R,11S)-11-Hydroxy-9-methyl-2-oxo-3-oxatricyclo[5.3.1.0⁴,¹¹]undec-1(10)-en-9-yl]-4-(hydroxymethyl)benzene-1-sulfonamide

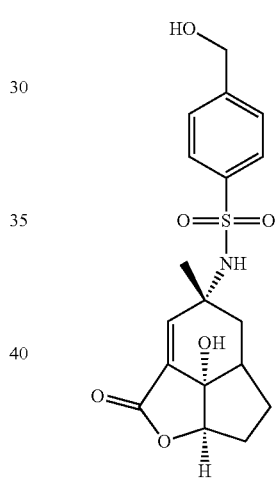

a) 4-(Bromomethyl)-N-[(4R,7R,9R,11S)-11-hydroxy-9-methyl-2-oxo-3-oxatricyclo[5.3.1.0⁴,¹¹]undec-1(10)-en-9-yl]benzene-1-sulfonamide A suspension of N-[(4R,7R,9R,11S)-11-Hydroxy-9-methyl-2-oxo-3-oxatricyclo[5.3.1.0⁴,¹¹]undec-1(10)-en-9-yl]-4-methylbenzene-1-sulfonamide (30.0 mg, 0.080 mmol) in carbon tetrachloride (3 mL) was evacuated and back-filled with nitrogen a couple of times. Then NBS (16.9 mg, 0.090 mmol) and AIBN (1.3 mg, 0.01 mmol) were added and the reaction was heated at reflux under nitrogen for 2 h. About 70% conversion (254 nm) and also some di-brominated product was formed (about 15%). The reaction was stopped and evaporated. Acetonitrile was added and the crude was purified by preparative HPLC (0.1% TFA 20 to 50/acetonitrile, ACE column). The collected fractions were extracted with CH$_2$Cl$_2$ (3×). The combined organic phases were washed with water and brine, dried (MgSO$_4$), filtered and concentrated to give 10.5 mg (27%) of the product.

LCMS (ESI$^+$) m/z 440, 442 [M−H]$^-$.

b) N-[(4R,7R,9R,11S)-1-Hydroxy-9-methyl-2-oxo-3-oxatricyclo[5.3.1.0$^{4,11}$]undec-1(10)-en-9-yl]-4-(hydroxymethyl)benzene-1-sulfonamide A solution of 4-(bromomethyl)-N-[(4R,7R,9R,11S)-11-hydroxy-9-methyl-2-oxo-3-oxatricyclo[5.3.1.0$^{4,11}$]undec-1(10)-en-9-yl]benzene-1-sulfonamide (7.35 mg, 0.02 mmol) in dry DMF (0.04 mL) was added to a stirred solution of AgBF$_4$ (4.21 mg, 0.02 mmol) in nitromethane (0.1 mL) under nitrogen. The reaction was stirred at room temperature overnight. Completed according to LCMS. (LCMS (ESI+) m/z 406 [M–H]–). Some of the benzylic alcohol was also observed in the first step (LCMS (ESI+) m/z 378 [M–H]–). The mixture was concentrated almost to dryness and methanol (0.2 mL) was added followed by oxalic acid (8.1 mg, 0.09 mmol) and the reaction stirred at room temperature under nitrogen for 2.5 h. Dissolved in acetonitrile and purified by preparative HPLC with acetonitrile (gradient from 5 to 45% in 12 min): TFA (aq 0.1%). Fractions contained product were collected and extracted with CH$_2$Cl$_2$ (3×). The organic phase was dried (MgSO4), filtered and concentrated under vacuum to give 3.2 mg (50%) of the title compound. 1H NMR (400 MHz, CDCl3): δ=7.61 (d, J=8.9 Hz, 2H), 6.87 (d, J=8.9 Hz, 2H), 6.20 (s, 1H), 5.18 (s, 1H), 4.82 (dd, J=8.1 Hz, J=2.1 Hz, 1H), 2.71 (dd, J=15.1 Hz, J=6.4 Hz, 1H), 2.46 (m, 1H), 2.03 (m, 1H), 1.95 (s, 2H), 1.76 (m, 1H), 1.65 (m, 2H), 1.31 (s, 3H), 1.23 (m, 1H). LCMS (ESI+) m/z 378 [M–H]–.

Example 23

N-[(4R,7R,9R,11 S)-11-Hydroxy-9-methyl-2-oxo-3-oxatricyclo[5.3.1.0$^{4,11}$]undec-1(10)-en-9-yl]-N,4-dimethylbenzene-1-sulfonamide

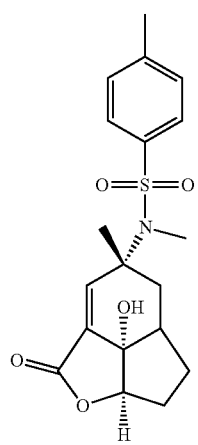

To a solution of N-[(4R,7R,9R,11S)-11-hydroxy-9-methyl-2-oxo-3-oxatricyclo[5.3.1.0$^{4,11}$]undec-1(10)-en-9-yl]-4-methylbenzene-1-sulfonamide (12.6 mg, 0.03 mmol) in DMF were added methyl iodide (0 mL, 0.0300 mmol) and potassium carbonate (4.79 mg, 0.03 mmol). The reaction mixture was stirred for 20 h at room temperature and then filtered through a pad of celite and concentrated to dryness to afford 12 mg (91%) of the title compound. $^1$H NMR (400 MHz, CDCl$_3$): δ=7.67 (d, J=8.4 Hz, 2H), 7.33 (d, J=8.4 Hz, 2H), 6.68 (s, 1H), 4.81 (dd, J=7.5 Hz, J=3.38 Hz, 1H), 2.95 (s, 3H), 2.73 (dd, J=14.9 Hz, J=6.4 Hz, 1H), 2.47 (m, 1H), 2.44 (s, 3H), 2.08 (m, 1H), 1.91 (m, 1H), 1.69-1.56 (m, 2H), 1.42 (s, 3H), 1.32 (s, 1H), LCMS (ESI$^+$) m/z 376 [M–H]$^-$.

Example 24

N-[(4R,7R,9R,11 S)-11-Hydroxy-9-methyl-2-oxo-3-oxatricyclo[5.3.1.0$^{4,11}$]undec-1(10)-en-9-yl]propane-2-sulfonamide 4.0 mg (12%), 314 [M–H]–

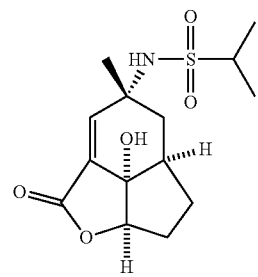

Example 25

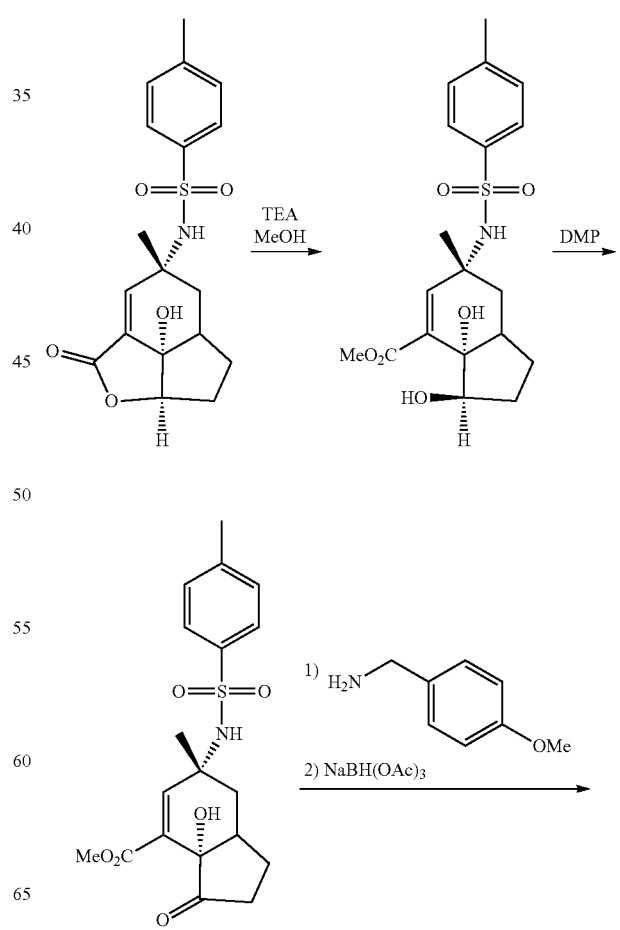

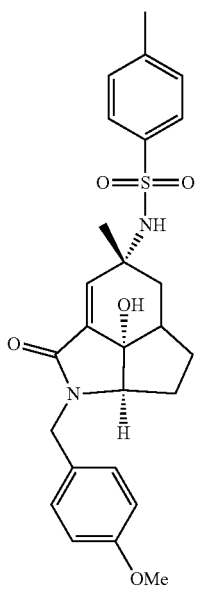

N-[(4R,7R,9R,11S)-11-hydroxy-3-[(4-methoxyphenyl)methyl]-9-methyl-2-oxo-3-azatricyclo[5.3.1.0⁴,¹¹]undec-1(10)-en-9-yl]-4-methylbenzene-1-sulfonamide

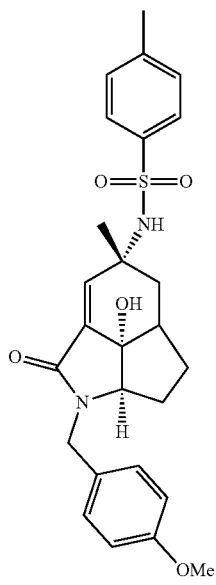

a) Methyl (3R,3aS,6R,7aR)-3,3a-dihydroxy-6-methyl-6-(4-methylbenzenesulfonamido)-2,3,3a,6,7,7a-hexahydro-1H-indene-4-carboxylate N-[(4R,7R,9R,11S)-11-hydroxy-9-methyl-2-oxo-3-oxatricyclo[5.3.1.0⁴,¹¹]undec-1(10)-en-9-yl]-4-methylbenzene-1-sulfonamide (83 mg, 0.23 mmol) was dissolved in dry methanol (0.5 mL) with 4 Å molecular sieves. Triethylamine (0.064 mL, 1.53 mmol) was added and the mixture was stirred at room temperature for 24 h. The residue was concentrated, dried under vacuum (8 h), to give the crude product (67% HPLC purity). The crude product was used directly in the next step without further purification. LCMS (ESI+) m/z 413 [M+OH+H]+, LCMS (ESI−) m/z 394 [M−H]−.

b) Methyl (3aS,6R,7aR)-3a-hydroxy-6-methyl-6-(4-methylbenzenesulfonamido)-3-oxo-2,3,3a,6,7,7a-hexahydro-1H-indene-4-carboxylate A crude reaction mixture of methyl (3R,3aS,6R,7aR)-3,3a-dihydroxy-6-methyl-6-(4-methylbenzenesulfonamido)-2,3,3a,6,7,7a-hexahydro-1H-indene-4-carboxylate (90 mg, 0.23 mmol) and Dess-Martin periodinane (DMP) (212 mg, 0.50 mmol) was dissolved in dry $CH_2Cl_2$ (0.5 mL). Then water (4 μL, 0.23 mmol) mixed with $CH_2Cl_2$ (0.1 mL) was slowly added. The clear solution became cloudy towards the end of the addition. The mixture was stirred at room temperature for 4 h. The residue was taken up in 30 mL of $CH_2Cl_2$ and washed with 15 mL of saturated aqueous $NaHCO_3$ solution, followed by 10 mL of water and 10 mL of brine. The organic layer was concentrated. Dissolved in acetonitrile and purified by preparative HPLC with acetonitrile (gradient from 5 to 45% in 12 min): 50 mM $NH_4HCO_3$/$NH_3$ pH 10. Fractions contained product were immediately collected and extracted with $CH_2Cl_2$ (3×10 mL). The organic phase was dried over magnesium sulfate and concentrated under vacuum, dried under vacuum, to give 41 mg (46%) of the title compound. LCMS (ESI+) m/z 411 [M+OH+H]+, LCMS (ESI−): m/z 392 [M−H]−.

c) N-[(4R,7R,9R,11S)-1-hydroxy-3-[(4-methoxyphenyl)methyl]-9-methyl-2-oxo-3-azatricyclo[5.3.1.0⁴,¹¹]undec-1(10)-en-9-yl]-4-methylbenzene-1-sulfonamide Methyl (3aS,6R,7aR)-3a-hydroxy-6-methyl-6-(4-methylbenzenesulfonamido)-3-oxo-2,3,3a,6,7,7a-hexahydro-1H-indene-4-carboxylate (41 mg, 0.10 mmol) was dissolved in THF (0.5 mL). (4-methoxyphenyl)methanamine (0.014 mL, 0.10 mmol) and acetic acid (0.06 mL, 0.10 mmol) were added. The reaction mixture was stirred in a capped flask at room temperature for 9 h. Sodium triacetoxyborohydride (24 mg, 0.11 mmol) was added and the mixture was stirred for additional 24 h at room temperature. Reaction mixture was concentrated, dissolved in acetonitrile and purified by preparative HPLC with acetonitrile (gradient from 5 to 45% in 12 min): 50 mM $NH_4HCO_3$/$NH_3$ pH 10. Fractions contained product were immediately collected and extracted with dichloromethane (3×10 mL). The organic phase was dried over magnesium sulfate and concentrated under vacuum, dried under vacuum (2 days), to give 5.5 mg (11%) of the title compound. ¹H NMR (400 MHz, $CDCl_3$) δ 7.65 (m, 2H), 7.26 (m, 2H), 7.12 (m, 1H), 6.79 (m, 1H), 6.13 (s, 1H), 4.70 (m, 1H), 4.10 (m, 1H), 3.76 (m, 1H), 3.74 (s, 1H), 3.72 (s, 3H), 3.67 (m, 1H), 2.62 (m, 1H), 2.36 (s, 3H), 2.35-2.31 (m, 1H), 1.74-1.63 (m, 2H), 1.51 (m, 1H), 1.47-1.36 (m, 1H), 1.26 (s, 3H). 1.21-1.18 (m, 1H).

LCMS (ESI+) m/z 483 [M+H]+, LCMS (ESI−) m/z 481 [M−H]−.

Example 26

N-[(4R,7R,9R,11S)-11-Hydroxy-3-[(4-methoxyphenyl)methyl]-9-methyl-2-oxo-3-azatricyclo[5.3.1.0⁴,¹¹]undec-1(10)-en-9-yl]-5-(trifluoromethyl)pyridine-2 sulfonamide a) Methyl (3R,3aS,6R,7aR)-3,3a-dihydroxy-6-methyl-6-[5-(trifluoromethyl)pyridine-2-sulfonamido]-2,3,3a,6,7,7a-hexahydro-1H-indene-4-carboxylate N-[(4R,7R,9R,11 S)-11-Hydroxy-9-methyl-2-oxo-3-oxatricyclo[5.3.1.0⁴,¹¹]undec-1(10)-en-9-yl]-5-(trifluoromethyl)pyridine-2-sulfonamide (320 mg, 0.76 mmol) was dissolved in dry methanol (2 mL) with 4 Å molecular sieves. Triethylamine (0.213 mL, 1.53 mmol) was added and the mixture was stirred at room temperature for 24 h. The residue was concentrated, dried under vacuum (8 h), to give the crude product (83% HPLC purity). The crude product was used directly in the next step without further purification. LCMS (ESI+) m/z 451 [M+H]+, LCMS (ESI−) m/z 449 [M−H]⁻.

b) Methyl (3aS,6R,7aR)-3a-hydroxy-6-methyl-3-oxo-6-[5-(trifluoromethyl)pyridine-2-sulfonamido]-2,3,3a,6,7,7a-hexahydro-1H-indene-4-carboxylate To a stirred mixture of methyl (3R,3aS,6R,7aR)-3,3a-dihydroxy-6-methyl-6-[5-(trifluoromethyl) pyridine-2-sulfonamido]-2,3,3a,6,7,7a-hexahydro-1H-indene-4-carboxylate (652 mg, 1.45 mmol) and AZADO (22 mg, 0.14 mmol) in CH₂Cl₂ (7.4 mL) and aqueous sat. NaHCO₃ (2.1 mL) containing KBr (17 mg, 0.14 mmol) and Bu₄NBr (75 mg, 0.23 mmol) was added dropwise a premixed solution (1:1.4 v/v) of aqueous NaOCl (12% Cl) (2.23 mL) and aqueous sat. NaHCO$_3$(3.2 mL) at 0° C. over 6 min. The mixture was vigorously stirred for 20 min at 0° C., then quenched with aqueous sat. Na$_2$S$_2$O$_3$ (4 mL). The aqueous layer was separated and extracted with CH$_2$Cl$_2$. The combined organic layers were washed with brine, dried over MgSO4, and concentrated under vacuum. The crude was purified by preparatory HPLC (ACE 5 C8 100×21.2 mm) with MeCN (gradient from 5 to 45% in 12 min): in TFA (aq) 0.1%. Fractions contained product were collected (immediately) and extracted with CH2Cl2 (3×10 mL). The organic phase was dried (MgSO$_4$) and concentrated under vacuum, dried over vacuum, to give the title compound, dried over vacuum, to give the title compound, (371 mg, 57% yield).

$^1$H NMR (400 MHz, CDCl$_3$): d=8.97 (s, 1H), 8.08 (m, 2H), 6.78 (m, 1H), 5.28 (s, 1H), 3.76 (s, 3H), 2.63-2.43 (m, 3H), 2.15 (m, 1H), 1.97 (m, 1H), 1.69-1.51 (m, 2H), 1.45 (s, 3H).

LCMS (ESI–): m/z=447 [M–H]– c) N-[(4R,7R,9R,11S)-11-Hydroxy-3-[(4-methoxyphenyl)methyl]-9-methyl-2-oxo-3-azatricyclo[5.3.1.0$^{4,11}$]undec-1(10)-en-9-yl]-5-(trifluoromethyl)pyridine-2 sulfonamide Methyl (3aS,6R,7aR)-3a-hydroxy-6-methyl-3-oxo-6-[[5-(trifluoromethyl)-2-pyridyl] sulfonylamino]-1,2,7,7a-tetrahydroindene-4-carboxylate (47 mg, 0.15 mmol) was dissolved in THF (2 mL). (4-Methoxyphenyl)methanamine (0.018 mL, 0.14 mmol) and titanium(IV)isopropoxide (0.040 mL, 0.14 mmol) were added. The reaction mixture was stirred in a capped flask at room temperature for 10 h. Sodium triacetoxyborohydride (28.9 mg, 0.14 mmol) was added and the reaction mixture was stirred for additional 24 h at room temperature. The reaction mixture was concentrated, dissolved in acetonitrile and purified by preparative HPLC with acetonitrile (gradient from 5 to 45% in 12 min): 50 mM NH$_4$HCO$_3$/NH$_3$ pH 10. Fractions contained product were immediately collected and extracted with dichloromethane (3×10 mL). The organic phase was dried over magnesium sulfate and concentrated under vacuum to give 20 mg (35%) the title compound.

$^1$H NMR (400 MHz, CDCl$_3$) δ 8.91 (m, 1H), 8.21 (m, 1H), 8.09 (d, J=8.2 Hz, 1H), 7.17 (m, 1H), 6.86 (m, 1H), 6.00 (s, 1H), 5.77 (brs, 1H), 4.74 (m, 1H), 4.09 (s, 1H), 3.80 (s, 3H), 3.67 (m, 1H), 2.69 (m, 1H), 2.42 (m, 1H), 1.82-1.69 (m, 2H), 1.64 (m, 1H), 1.47 (s, 3H), 1.39-1.29 (m, 2H).

LCMS (ESI+) m/z 538[M+H]+, LCMS (ESI–) m/z 536 [M–H]–.

Example 27

N-[(4R,7R,9R,11S)-3-[(4-Cyanophenyl)methyl]-11-hydroxy-9-methyl-2-oxo-3-azatricyclo[5.3.1.0$^{4,11}$]undec-1 (10)-en-9-yl]-5-(trifluoromethyl)pyridine-2-sulfonamide

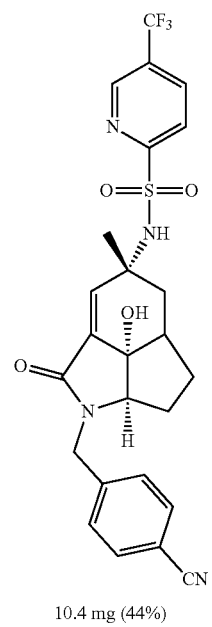

10.4 mg (44%)

LCMS (ESI–) m/z=531 [M–H]–

$^1$H NMR (400 MHz, CDCl$_3$): δ=8.93 (brs, 1H), 8.22 (m, 1H), 8.09 (m, 1H), 7.64 (m, 2H), 7.36 (m, 2H), 6.04 (s, 1H), 5.60 (s, 1H), 4.87 (m, 1H), 4.21 (m, 1H), 3.69 (m, 1H), 2.73 (m, 1H), 2.45 (m, 1H), 1.86-1.71 (m, 3H), 1.71 (m, 1H), 1.47 (s, 3H), 1.40-1.31 (m, 1H).

Example 28

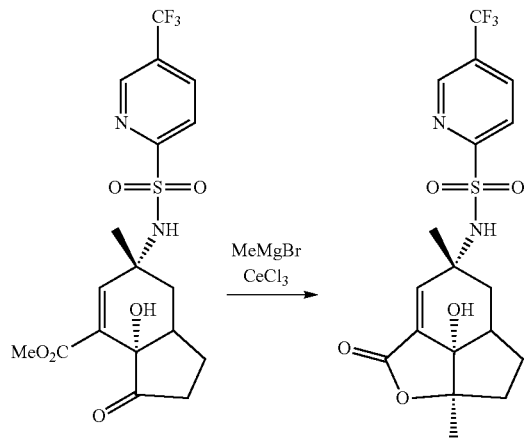

N-[(4R,7R,9R,11S)-11-hydroxy-4,9-dimethyl-2-oxo-3-oxatricyclo[5.3.1.0$^{4,11}$]undec-1(10)-en-9-yl]-5-(trifluoromethyl)pyridine-2-sulfonamide

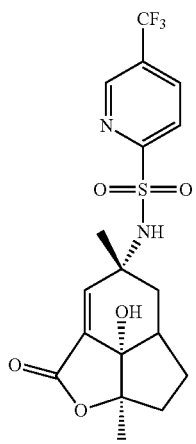

N-[(4R,7R,9R,11S)-11-hydroxy-9-methyl-2-oxo-3-oxatricyclo[5.3.1.0$^{4,11}$]undec-1(10)-en-9-yl]-5-(trifluoromethyl)pyridine-2-sulfonamide (10 mg, 0.022 mmol) and cerium(III)chloride (anhydrous) (17 mg, 0.067 mmol) were mixed in THF (2 mL) under nitrogen and the resulting mixture was cooled to −78° C. Methylmagnesium bromide (3M in Et$_2$O) (45 uL, 0.13 mmol) was added drop-vise at −78° C. The reaction mixture was stirred in capped flask at room temperature for 24 h. Reaction mixture was purified with preparative TLC (Heptane:EtOAc 1:1) and product band was isolated and extracted with MeCN filtrated concentrated under vacuum, dried over vacuum, to give the title compound, (1.05 mg, 11% yield).

$^1$H NMR (400 MHz, CDCl$_3$): δ=8.94 (s, 1H), 8.19 (m, 1H), 8.04 (m, 1H), 6.10 (s, 1H), 5.58 (s, 1H), 2.77 (m, 1H), 2.46 (m, 1H), 1.94-1.70 (m, 4H), 1.50 (s, 3H), 1.48 (s, 3H), 1.20-1.16 (m, 1H).

LCMS (ESI+): LCMS (ESI−): m/z=431 [M−H]−

BIOLOGICAL EXAMPLE

Selected example compounds were evaluated in vitro in cellular assays including a STAT3 Luciferase reporter gene assay.

Anti-STAT3 Activity of Example Compounds

STAT3 Luciferase Reporter Gene Assay

The ability to inhibit STAT3 signaling of the example compounds in comparison to galiellalactone was evaluated using a STAT3 Luciferase reporter gene assay.

Compounds were tested for dose response activity to determine IC$_{50}$ at eight different doses (0.03, 0.1, 0.3, 1, 3, 10, 30 and 100 μM) in triplicate on the STAT3 reporter system.

Briefly, the STAT3 reporter/HEK293 cell line was plated in 96-well white plates for 16 h. Cells were pretreated with compounds for 1 h. Cells were then treated with IL-6 to induce STAT3 activation for 16 h. Luciferase activity was measured and analyzed.

The results are presented in Table 5 below as IC$_{50}$-values.

TABLE 5

| | | | | | | |
|---|---|---|---|---|---|---|
| Inhibition of STAT3 signaling. | | | | | | |
| Example | IC50 (μM) | Cy$_1$ | R$_5$ | A | R$_6$ | X |
| Galiellalactone | 7.5 | — | — | — | H | "O" |
| 1 | 1.1 | Phenyl | 4-Me | — | H | "O" |
| 2 | 3.0 | Phenyl | 4-H | — | H | "O" |
| 3 | 8.41 | Phenyl | 4-OMe | — | H | "O" |
| 4 | 6.71 | Phenyl | 2-NO$_2$ | — | H | "O" |
| 5 | 1.76 | Phenyl | 4-CF3 | — | H | "O" |
| 6 | 6.76 | Phenyl | 3-Me | — | H | "O" |
| 7 | 4.69 | Phenyl | 2-F | — | H | "O" |
| 8 | 5.05 | Phenyl | 4-NO$_2$ | — | H | "O" |
| 9 | 9.31 | Phenyl | 4-CN | — | H | "O" |
| 10 | 3.2 | Phenyl | 4-Br | — | H | "O" |
| 11 | 0.24 | Phenyl | 4-dihydrooxazole | — | H | "O" |
| 12 | 3.38 | -2-pyridyl | 4-Me | — | H | "O" |
| 13 | 5.65 | -3-pyridyl | 4-Me | — | H | "O" |
| 14 | 6.78 | -2-thiophene | 5-Me | — | H | "O" |
| 15 | 2.9 | Phenyl | 2-Cl, 4-CF3 | — | H | "O" |
| 16 | 4.5 | Phenyl | 3-F, 4-Me | — | H | "O" |
| 17 | 3.16 | Phenyl | 4-F | — | H | "O" |
| 18 | 2.26 | Phenyl | 4-Cl | — | H | "O" |
| 19 | 9.69 | Phenyl | 4-Me | —CH2— | H | "O" |
| 20 | 1.25 | -2-pyridyl | 4-CF3 | — | H | "O" |
| 21 | 3.63 | Phenyl | 4-NH2 | — | H | "O" |
| 22 | 11.4 | Phenyl | 4-CH2OH | — | H | "O" |
| 23 | inactive | Phenyl | 4-Me | — | H | "O" |
| 24 | 97 | na | na | — | H | "O" |
| 25 | 3.70 | Phenyl | 4-Me | — | H | NCH$_2$PhOMe |
| 26 | 8.64 | -2-pyridyl | 4-CF3 | — | H | NCH$_2$PhOMe |
| 27 | 8.61 | -2-pyridyl | 4-CF3 | — | H | NCH$_2$PhCN |
| 28 | 0.92 | -2-pyridyl | 4-CF3 | — | Me | "O" |

As can be seen in Table 5, several of the examples showed increased potency compared to galiellalactone. Also, as seen in table 5 there is a clear structure activity relationship and certain structural modifications result in significantly reduced or total loss of activity in the STAT3 reporter assay (examples 23 and 24). This indicates a specific binding to the STAT3 protein.

Compounds wherein Cy1 is phenyl, pyridyl or thienyl and $R_5$ is a methyl, chlorine or trifluoromethyl in the para position have been found to be of particular interest, as the presence of these substituents seemingly increase the potency. As can be seen in Table 1 above, example 1 ($R_5$=methyl) provides a compound with lower IC50 value than the parent compound galiellelactone. Compounds wherein $R_5$ is a methyl, chlorine or trifluoromethyl in the para position are thus preferred according to some embodiments. In such embodiments, $R_1$ is typically methyl. Further, alkyl sulfonamides (cf. example 23 compound) as well as N-substituted sulfonamides (cf. example 24 compound) were found to have no or low activity, suggesting the importance of the cyclic substituent as well as the nitrogen being unsubstituted.

In order to further assess the properties of the sulfonamide analogues of galiellalactone, and to show that increased STAT3 inhibition potency translates into increased inhibition of the proliferation of cancer cells dependent on STAT3 signaling, IL-6 stimulated LNCaP prostate cancer cells were treated with example 1.

TABLE 6

Inhibition of IL-6 stimulated LNCaP cell proliferation as measured in a MTT assay.

| Example No. | GIC50 (uM) |
|---|---|
| Galiellalactone | 2.8 |
| 1 | 1.0 |

It was found that example 1 (cf. Table 6) has increased ability to inhibit proliferation of IL-6 stimulated LNCaP prostate cancer cells compared to galiellalactone. This finding is coherent with the data in table 1 and further supports that novel sulfonamide analogues are more potent in blocking proliferation of STAT3 dependent STAT3 cells than galiellalactone.

Thus an embodiment relates to compounds and pharmaceutical compositions disclosed herein, e.g. compounds according to formula (I) or preferred selections thereof, for inhibiting the activity of a STAT3 receptor with equal or greater potency than galiellalactone.

Western Blot Analysis of pSTAT3 in Prostate Cancer Cells

Samples were separated on 7.5% precast gel (Mini-PROTEAN TGX; Bio-Rad) or 8% Tris Bis self cast gels. The gels were blotted onto PVDF membranes and blocked with 5% milk or 5% BSA. Membranes were incubated with primary antibody diluted in 5% milk or 5% BSA for 1 h at room temperature or overnight at 4° C. with antibodies raised against STAT3 and pSTAT3 tyr-705 (Cell Signaling Technology). After incubation with secondary anti-mouse or anti-rabbit antibody conjugated with horseradish peroxidase (GE Healthcare Life Sciences) the membrane was treated with enhanced chemiluminescent reagent (Santa Cruz Biotechnology or Millipore) followed by exposure to X-Ray film or visualized using a Chemidoc XRS system (Bio-Rad).

BRIEF DESCRIPTION OF THE DRAWINGS

FIG. 1 shows an image of the Western blot analysis of p-STAT3(tyr705) and total STAT3 in LNCaP-IL6 and LNCaP prostate cancer cell lines.

As shown in FIG. 1, only LNCaP-IL6 cells express active pSTAT3. This shows that LNCaP-IL6 is a STAT3 driven cell line whereas LNCaP is a non-STAT3 driven cell line as pSTAT3 is a driver of proliferation.

In Vivo Pharmacokinetics

Pharmacokinetic (PK) studies were performed in CD1 mice to establish plasma exposure following administration of single oral doses of galiellalactone (GL) and example 1. Sample analysis was by LC-MS/MS. Dose solutions were prepared at a drug concentration of 0.5 mg/mL in 5% DMSO in 50 mM citrate buffer (citric acid/sodium citrate pH 4.0) and administered as a 20 mL/kg oral gavage (10 mg/kg).

Following oral administration at 10 mg/kg quantifiable concentrations were detected in at least one animal from each time point out to the final 8 hour samples, $T_{max}$ was the first time point in all cases suggesting rapid absorption from the gut.

TABLE 7

In vivo pharmacokinetic properties

| | Compound | |
|---|---|---|
| PK Parameter | GL | Example 1 |
| $C_{max}$ (ng/mL) | 52 | 129 |
| $T_{max}$ (h) | 0.5 | 0.25 |
| Apparent half-life (h) | 1.2 | 2.0 |
| AUC 0-t (ng/mL · h) | 82 | 141 |
| AUC 0-∞ (ng/mL · h) | 87 | 157 |

Higher exposure was measured for example 1 compared to GL, suggesting improved bioavailability for this compound (table 7).

This confirms that the addition of a sulfonamide moiety in the 4 position not only influences the STAT3 inhibitory potency but can also improve the drug-like properties significantly.

Chemical Stability

The chemical stability of example 20 and 28 in solution was determined in phosphate buffer solution (PBS) at 37° C. as outlined below.

A 4 μl volume of 100 μM stock solution of the study compound in 50% DMSO was added to 396 μl of PBS, to obtain 1 μM test concentration. The study compounds were incubated in PBS at 37° C. with 600 rpm shaking. The incubations were quenched (30, 60, and 120 min) using a two-fold volume of cold acetonitrile and analyzed. The samples (0, 30, 60, and 120 min) were analyzed using a Waters Acquity UPLC with Thermo Q-Exactive Focus Orbitrap and a Waters HSS T3 (2.1×50 mm, 1.7 μm particle size) column.

It was found that example 20 had a $t_{1/2}$ of 349 minutes, whereas the $t_{1/2}$ for example 28 exceeded 789 min.

As can be seen the addition of a methyl group ($R_6$=Me) significantly increases the chemical stability. This observed effect most likely arises from an increased stability of the lactone ring towards hydrolysis.

The invention claimed is:

1. A compound according to formula (I),

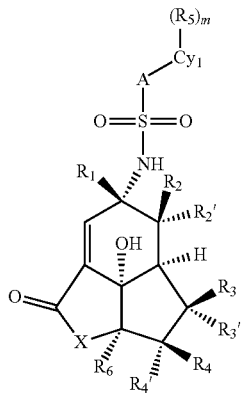

wherein:

"X" is selected from the group consisting of O, NH, NC1-5 alkylene-aryl, NC1-5 alkylene-heteroaryl, N-aryl, NC1-C3 alkyl, and NC(O)C1-C3 alkyl, wherein said aryl is unsubstituted or substituted with one or several substituents independently selected from the group consisting of C1-C5 alkyl, C1-5 fluoroalkyl, halo, OH, OC1-5 alkyl, C1-5 alkyleneOC1-5 alkyl, cyano, NH, NHC1-5 alkyl, N(C1-5 alkyl)$_2$, in which the C1-5 alkyl may be the same or different, and nitro, and wherein said heteroaryl is unsubstituted or substituted with one or several substituents independently selected from the group consisting of C1-C5 alkyl, C1-5 fluoroalkyl, halo, oxo, OH, OC1-5 alkyl, C1-5 alkyleneOC1-5 alkyl, cyano, NH, NHC1-5 alkyl, N(C1-5 alkyl)$_2$, in which the C1-5 alkyl may be the same or different, and nitro;

$R_1$ is selected from the group consisting of hydrogen, C1-C5 alkyl, C1-C5 fluoroalkyl, and

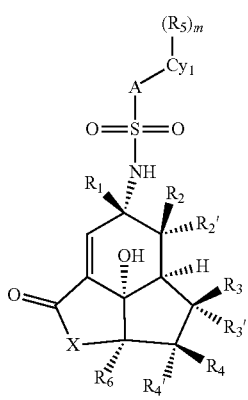

wherein

"B" is C1-C5 alkylene;

"C" is selected from the group consisting —O—, —NH—, —C(O)O—, —OC(O)—, —OSO$_2$—, —NHSO$_2$—, —C(O)NR$_{11}$—, and —N(R$_{11}$)C(O)—, wherein R$_{11}$ is H or C1-C4 alkyl; and "D" is selected from the group consisting of hydrogen, C1-C5 alkyl, C1-C5 fluoroalkyl, and -ECy$_2$, provided that "D" is not hydrogen if "C" is —OSO$_2$— or —NHSO$_2$—, wherein "E" is a direct bond or a C1-C5 alkylene, and Cy$_2$ is aryl or heteroaryl, wherein Cy$_2$ is unsubstituted or substituted with one or several substituents independently selected from the group consisting of C1-5 alkyl, C1-5 fluoroalkyl, halo, OH, OC1-5 alkyl, nitro, cyano, NH, NHC1-5 alkyl, and N(C1-5 alkyl)$_2$, in which the C1-5 alkyl may be the same or different;

$R_2$, $R_2'$, $R_3$, and $R_3'$ are independently selected from the group consisting of H, F, OH, C1-5 alkyl, and C1-5 fluoroalkyl $R_4$ and $R_4'$ are independently selected from the group consisting of H, C1-5 alkyl, halo, and G-Cy$_3$, wherein "G" is a bond or methylene, and Cy$_3$ is aryl or a 5- or 6-membered heteroaryl, wherein Cy$_3$ is unsubstituted or substituted with a one or several substituents independently selected from the group consisting C1-5 alkyl, C1-5 fluoroalkyl, halo, OH, OC1-5 alkyl, C1-5 alkyleneOC1-5 alkyl, nitro, cyano, NH$_2$ and N(C1-5 alkyl)$_2$, in which the C1-5 alkyl may be the same or different;

"A" is independently selected from the group consisting of a bond, C1-5 alkylene, NH, NC1-5 alkyl, C1-3 alkyleneN(R$_{10}$)C1-5 alkylene, and N(R$_{10}$)C1-3 alkylene, wherein R$_{10}$ is H or C1-C4 alkyl;

Cy$_1$ is selected from the group consisting of 5 and 6-membered monocyclic heteroaryls, phenyl, bicyclic heteroaryls, wherein one or both rings are aromatic, naphthyl, 3- to 8-membered non-aromatic heterocycles, and C3-8 non-aromatic carbocycles;

"m" is an integer being 0 (zero), 1, 2, 3, 4, or 5;

$R_5$ is independently selected from the group consisting of C1-8 alkyl, C1-5 fluoroalkyl, halo, cyano, methylene cyano, OH, OC1-5 alkyl, C1-8 alkyleneOH, C1-8 alkyleneOC1-5 alkyl, SH, SC1-5 alkyl, SO$_2$C1-5 alkyl, C1-3 alkyleneSO$_2$C1-5 alkyl, OC1-3 fluroalkyl, C1-3 alkyleneOC1-3 fluroalkyl, NH2, NHC1-3 alkyl, N(C1-5 alkyl)$_2$, in which the C1-5 alkyl may be the same or different, C1-3 alkyleneNH2, C1-3 alkyleneNHC1-3 alkyl, C1-3 alkyleneN(C1-5 alkyl)$_2$, in which the C1-5 alkyl may be the same or different, C(O)OH, C(O)OC1-5 alkyl, C1-3 alkyleneC(O)OH, C1-3 alkyleneC(O)OC1-5 alkyl, OC(O)C1-5 alkyl, C1-3 alkyleneOC(O)C1-5 alkyl, NHC(O)C1-3 alkyl, N(C1-3 alkyl)C(O)C1-3 alkyl, C1-3 alkyleneNHC(O) C1-3 alkyl, C1-3 alkyleneN(C1-3 alkyl)C(O)C1-3 alkyl, C(O)NH$_2$, C(O)NHC1-3 alkyl, C(O)N(C1-5 alkyl)$_2$, in which the C1-5 alkyl may be the same or different, C1-3 alkyleneC(O)NH$_2$, C1-3 alkyleneC(O) NHC1-3 alkyl, C1-3 alkyleneC(O)N(C1-5 alkyl)$_2$, in which the C1-5 alkyl may be the same or different, nitro, C(O)C1-C5 alkyl, NHSO$_2$C1-C3 alkyl, N(C1-C3 alkyl)SO$_2$C1-C3 alkyl, NHSO$_2$C1-C3 fluoroalkyl, N(C1-C3 alkyl)SO$_2$C1-C3 fluoroalkyl, OC2-C3alkyleneN(C1-C3 alkyl)$_2$, in which the C1-C3 alkyl may be the same or different, and C3-8 non-aromatic carbocycles;

if Cy$_1$ is a 3- to 8-membered non-aromatic heterocycle or a C3-8 non-aromatic carbocycle and "m" is at least 2, then two R$_5$, being attached to the same carbon atom on said 3- to 8-membered non-aromatic heterocycle or said C3-8 non-aromatic carbocycle, may be connected to each other to form a 3, 4 or 5-membered spiro ring; said spiro ring being a non-aromatic carbocycle or a non-aromatic heterocycle;

if Cy$_1$ is a 3- to 8-membered non-aromatic heterocycle or a C3-8 non-aromatic carbocycle and "m" is at least 2, then two R$_5$, being attached to different atoms in said 3- to 8-membered non-aromatic heterocycle or said C3-8 non-aromatic carbocycle, may be connected to each other to form a bond or C1-5 alkylene bridge; Cy$_1$ thus being a bicyclic residue;

if Cy$_1$ is a monocyclic heteroaryl, a bicyclic heteroaryl, a 3- to 8-membered non-aromatic heterocycle, or a C3-8 non-aromatic carbocycle, then R$_5$ may be a double bonded oxygen (═O), being attached to a carbon or sulfur atom in said heteroaryl or cycle; and R$_6$ is selected from the group consisting of hydrogen and C1-C5 alkyl.

2. The compound according to claim 1, wherein
R$_1$ is independently selected from the group consisting of hydrogen, methyl, C1fluoroalkyl, and

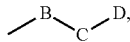

wherein
"B" is methylene;
"C" is selected from the group consisting —O—, —NH—, —C(O)O—, —OC(O)—, —NHSO$_2$—, —C(O)NR$_{11}$—, and —N(R$_{11}$)C(O)—, wherein R$_{11}$ is H or C1-C3 alkyl; and
"D" is selected from the group consisting of hydrogen C1-C3 alkyl, C1-C3 fluoroalkyl and -ECy$_2$, provided that "D" is not hydrogen if "C" is —NHSO$_2$—, wherein "E" is a direct bond or a methylene, and Cy$_2$ is aryl or heteroaryl, wherein Cy$_2$ is unsubstituted or substituted with one or several substituents independently selected from the group consisting of methyl, C1 fluoroalkyl, halo, OH, OC1-5 alkyl, cyano, NH$_2$, NHC1-5 alkyl, and N(C1-5 alkyl)$_2$, in which the C1-5 alkyl may be the same or different.

3. The compound according to claim 1, wherein
R$_2$, R$_2$', R$_3$ and R$_3$' are independently selected from the group consisting of H, F, and OH;
R$_4$ and R$_4$' are independently selected from the group consisting of H, methyl, and G-Cy$_3$, wherein "G" is a bond or methylene, and Cy$_3$ is an unsubstituted aryl; and
R$_6$ is hydrogen or methyl.

4. The compound according to claim 1, wherein "A" is selected from the group consisting of a bond and methylene.

5. The compound according to claim 1, wherein Cy$_1$ is selected from the group consisting of phenyl, 5-membered heteroaryls selected from the group consisting of furan, thiophene, oxazole, thiazole, isoxazole, and oxadiazole, and 6-membered heteroaryls.

6. The compound according to the claim 5, wherein Cy$_1$ is selected from the group consisting of phenyl, thiophenyl, furanyl, pyridinyl, pyrimidinyl, pyridazinyl, pyrazinyl, oxazolyl, isoxazolyl, oxadiazolyl, isothiazolyl, and thiazolyl.

7. The compound according to claim 1, wherein the integer "m" is 1, 2, 3, 4, or 5.

8. The compound according to claim 7, wherein R$_5$ is selected from the group consisting of methyl, C1 fluoroalkyl, halo, cyano, OH, -OMe, C1-2 alkyleneOH, SO$_2$C1-3 alkyl, OC1 flurorolkyl, NH$_2$, NHC1-3 alkyl, N(C1-3 alkyl)$_2$, in which the C1-3 alkyl may be the same or different, C(O)OH, C(O)OC1-3 alkyl, NHC(O)C1-3 alkyl, N(C1-3 alkyl)C(O)C1-3 alkyl, C(O)NH$_2$, C(O)NHC1-3 alkyl, C(O)N(C1-3 alkyl)$_2$, in which the C1-3 alkyl may be the same or different, C(O)C1-C3 alkyl, NHSO$_2$C1-3 alkyl, N(C1-C3 alkyl)SO$_2$C1-3 alkyl, OC2-C3alkyleneN(C1-C3 alkyl)$_2$, in which the C1-3 alkyl may be the same or different, and C3-8 non-aromatic carbocycles.

9. The compound according claim 8, wherein R$_5$ is selected from the group consisting of methyl, —NH$_2$, fluorine, —CF$_3$, —CHF$_2$, bromine, and chlorine.

10. The compound according to claim 1, wherein R$_1$ is selected from the group consisting of methyl, CH$_2$OH, and CH$_2$OC1-C3 alkyl.

11. The compound according to claim 1, wherein R$_2$, R$_2$', R$_3$, and R$_3$' all are hydrogen.

12. The compound according to claim 1, wherein both R$_4$ and R$_4$' are hydrogen.

13. The compound according to claim 1, wherein "X" is selected from the group consisting of O and NCH$_2$phenyl, wherein said phenyl is unsubstituted or substituted with one or several substituents independently selected from the group consisting of methyl, CF$_3$, halo, OH, OMe, CH$_2$OCMe, cyano, NH, NHMethyl, and N(Methyl)$_2$, and nitro.

14. The compound according to claim 1, wherein said compound is selected from the group consisting of:

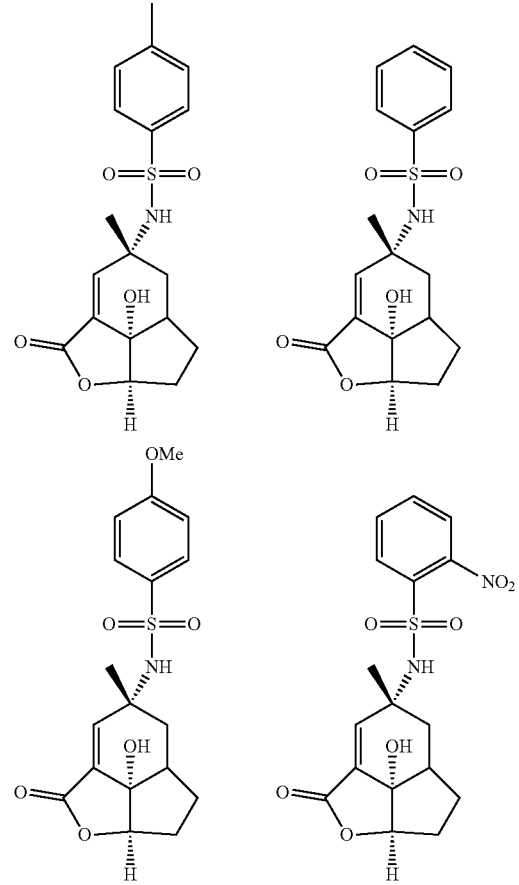

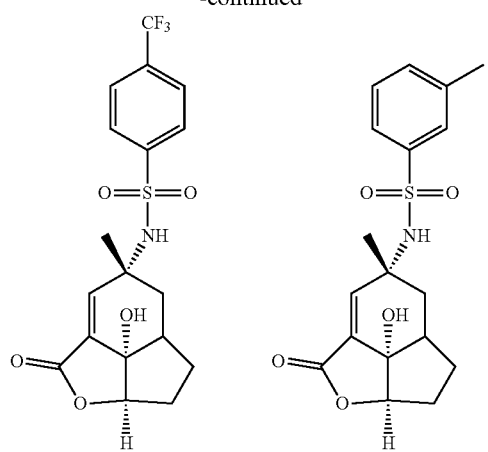
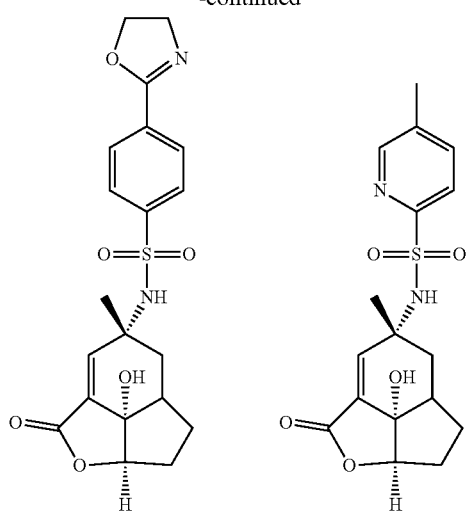
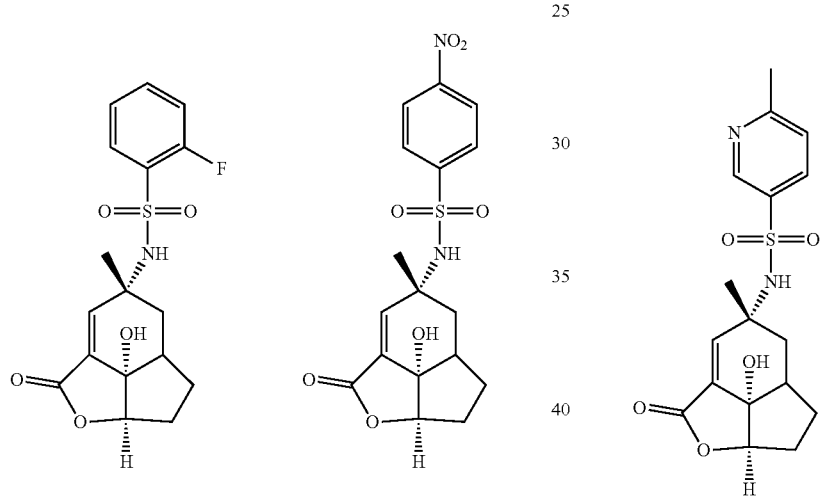
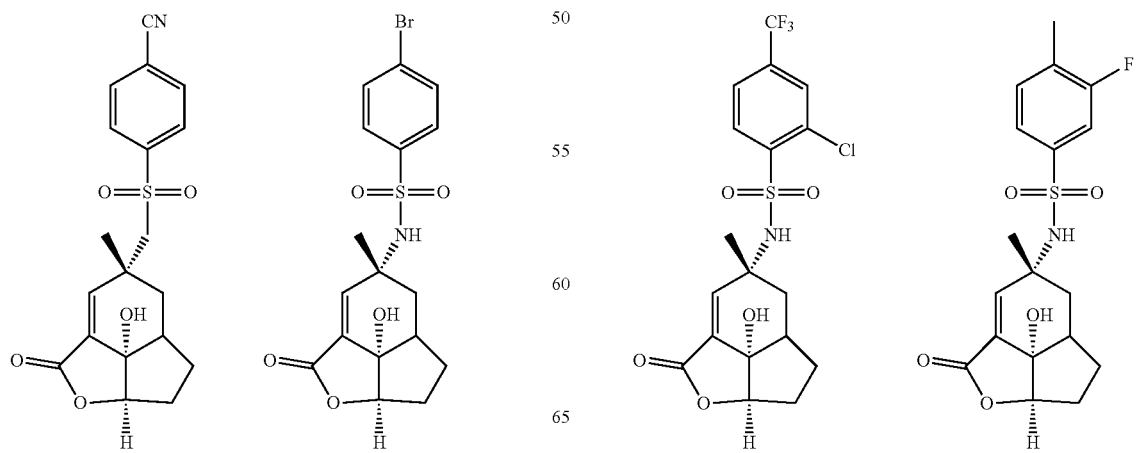

79
-continued
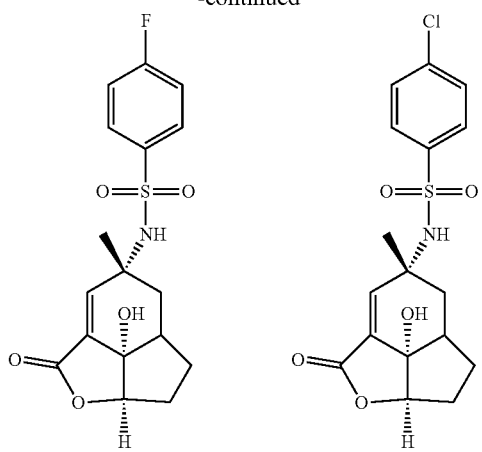
80
-continued
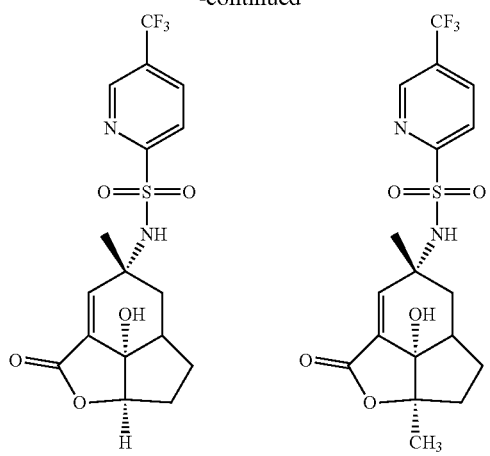
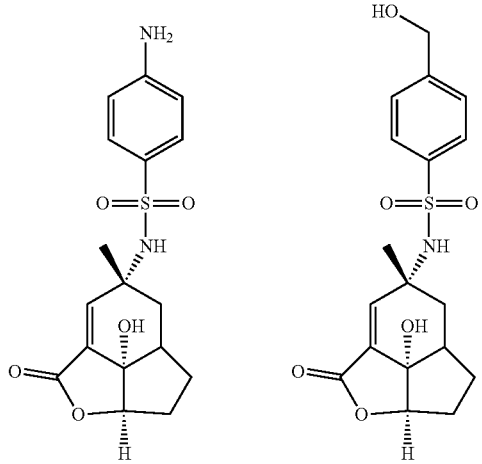
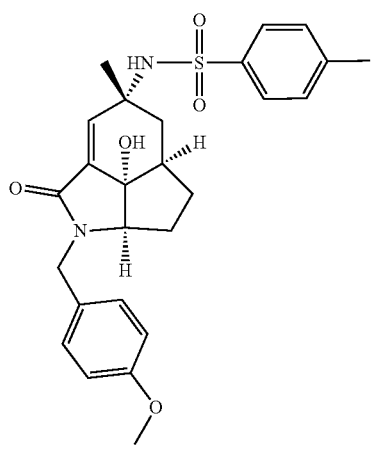
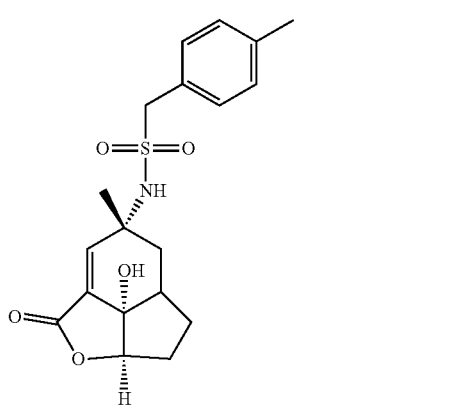
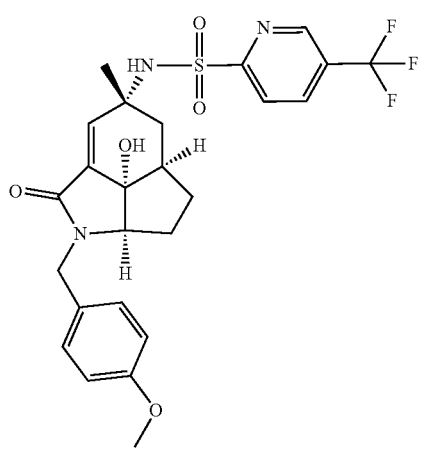

-continued

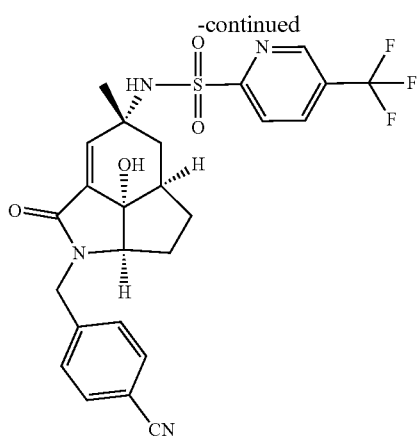

wherein the indicated stereochemistry is relative or absolute stereochemistry.

15. A pharmaceutical composition comprising a compound according to claim 1, and at least one pharmaceutically acceptable carrier or excipient.

16. The pharmaceutical composition according to claim 15, wherein said composition further comprises at least one additional therapeutic agent, said additional therapeutic agent being selected from the group consisting of Abraxane, Abiraterone, Aldesleukin, Alemtuzumab, Aminolevulinic Acid, Anastrozole, Aprepitant, Arsenic Trioxide, Azacitidine, Bendamustine Hydrochloride, Bevacizumab, Bexarotene, Bortezomib, Bleomycin, Cabazitaxel, Capecitabine, Carboplatin, Cetuximab, Cisplatin, Clofarabine, Crizotinib, Cyclophosphamide, Cytarabine, Dacarbazine, Dasatinib, Daunorubicin Hydrochloride, Decitabine, Degarelix, Denileukin Diftitox, Dexrazoxane Hydrochloride, Docetaxel, Doxorubicin Hydrochloride, Doxorubicin Hydrochloride Liposome, Eltrombopag Olamine, Enzalutamide, Epirubicin Hydrochloride, Erlotinib Hydrochloride, Etoposide, Etoposide Phosphate, Everolimus, Exemestane, Filgrastim, Fludarabine Phosphate, Fluorouracil, Fulvestrant, Gefitinib, Gemcitabine Hydrochloride, Ibritumomab Tiuxetan, Imatinib Mesylate, Imiquimod, Irinotecan Hydrochloride, Ixabepilone, Lapatinib Ditosylate, Lenalidomide, Letrozole, Leucovorin Calcium, Leuprolide Acetate, Liposomal Cytarabine, Methotrexate, Nelarabine, Nilotinib, Ofatumumab, Oxaliplatin, Paclitaxel, Palifermin, Palonosetron Hydrochloride, Panitumumab, Pazopanib Hydrochloride, Pegaspargase, Pemetrexed Disodium, Plerixafor, Pralatrexate, Raloxifene Hydrochloride, Rasburicase, Recombinant HPV Bivalent Vaccine, Recombinant HPV Quadrivalent Vaccine, Rituximab, Romidepsin, Romiplostim, Sipuleucel-T, Sorafenib Tosylate, Sunitinib Malate, Talc, Tamoxifen Citrate, Tasquinimod, TAK700, Temozolomide, Temsirolimus, Thalidomide, Topotecan Hydrochloride, Toremifene, Tositumomab and I 131 Iodine Tositumomab, Trastuzumab, Vincristine Sulfate, Vorinostat, ARN-509, ODM-201, custirsen, AT 101, cisplatin, abozantinib, dasatinib, MK2206, axitinib, saracatinib, tivantinib, linsitinib, GSK2636771, BKM120, Vorinostat, panobinostat, azacitidine, IPI-504, STA9090, lenalidomid, OGX-427, Zoledronic Acid and Xofigo, MEDI4736, tremelimumab, ipilimumab, Pembrolizumab, Nivolumab, Durvalumab, and Atezolizumab.

17. A method of treating a disease or disorder comprising administering to a subject an effective amount of a compound according to claim 1, wherein the disease or disorder is selected from the group consisting of: solid cancers, hematological cancers, benign tumors, hyperproliferative diseases, inflammations, autoimmune diseases, graft or transplant rejections, delayed physiological function of grafts or transplants, neurodegenerative diseases and viral infections.

18. A method of inhibiting the activity of the STAT3 transcription factor with greater potency than galiellalactone, the method comprising administering an effective amount of a composition according to claim 1 to a subject in need thereof.

19. The compound according to claim 1, wherein "X" is O.

* * * * *